United States Patent
Matsuda

(10) Patent No.: US 10,722,213 B2
(45) Date of Patent: Jul. 28, 2020

(54) ULTRASONIC DEVICE, ULTRASONIC MODULE, AND ULTRASONIC MEASUREMENT APPARATUS

(71) Applicant: Seiko Epson Corporation, Tokyo (JP)

(72) Inventor: Hiroshi Matsuda, Gifu (JP)

(73) Assignee: Seiko Epson Corporation (JP)

( * ) Notice: Subject to any disclaimer, the term of this patent is extended or adjusted under 35 U.S.C. 154(b) by 614 days.

(21) Appl. No.: 15/240,226

(22) Filed: Aug. 18, 2016

(65) Prior Publication Data
US 2017/0055949 A1     Mar. 2, 2017

(30) Foreign Application Priority Data
Aug. 31, 2015   (JP) ................... 2015-170531

(51) Int. Cl.
*A61B 8/00*    (2006.01)
*A61B 8/14*    (2006.01)
(Continued)

(52) U.S. Cl.
CPC .......... *A61B 8/4488* (2013.01); *A61B 8/4427* (2013.01); *A61B 8/5207* (2013.01);
(Continued)

(58) Field of Classification Search
CPC ... A61B 8/4488; A61B 8/5207; A61B 8/4427; A61B 8/54; A61B 8/4494; A61B 8/145; A61B 8/14; A61B 8/0825; A61B 8/15; A61B 8/406; A61B 8/42; B06B 1/0622; G01S 7/52079; G01S 15/8915; G01S 7/52038; G01S 7/52046
See application file for complete search history.

(56) References Cited

U.S. PATENT DOCUMENTS 5,651,365 A * 7/1997 Hanafy ................ G10K 11/345
                                                    29/25.35
5,724,976 A * 3/1998 Mine ..................... B06B 1/0614
                                                    600/459
(Continued)

FOREIGN PATENT DOCUMENTS

JP       2011-010794 A       1/2011
JP       2011-072585 A       4/2011
(Continued)

OTHER PUBLICATIONS

Matte et al. "Optimization of a Phased-Array Transducer for Multiple Harmonic Imaging in Medical Applications: Frequency and Topology," Mar. 2011, IEEE Transactions on Ultrasonics Ferroelectrics, and Frequency Control, vol. 58, No. 3 (Year: 2011).*

*Primary Examiner* — Baisakhi Roy
(74) *Attorney, Agent, or Firm* — Harness, Dickey & Pierce, P.L.C.

(57) ABSTRACT

An ultrasonic device includes a plurality of ultrasonic wave transmitting sections adapted to transmit an ultrasonic wave as a fundamental wave, and a plurality of ultrasonic wave receiving sections capable of receiving a second-order harmonic wave with respect to the fundamental wave, the plurality of ultrasonic wave transmitting sections and the plurality of ultrasonic wave receiving sections are arranged along an X direction, the plurality of ultrasonic wave receiving sections are arranged at first intervals corresponding to the order of the second-order harmonic wave, the N ultrasonic wave transmitting sections constitute a single transmission channel, and are wired with each other, and the transmission channels are arranged at second intervals each twice as long as the first interval. N is a natural number.

12 Claims, 13 Drawing Sheets

(51) Int. Cl.
  *G01S 15/89* (2006.01)
  *G01S 7/52* (2006.01)
  *B06B 1/06* (2006.01)
  *A61B 8/08* (2006.01)

(52) U.S. Cl.
  CPC ........ *B06B 1/0622* (2013.01); *G01S 7/52038* (2013.01); *G01S 7/52046* (2013.01); *G01S 7/52079* (2013.01); *G01S 15/8915* (2013.01); *A61B 8/145* (2013.01); *A61B 8/4494* (2013.01); *A61B 8/54* (2013.01)

(56) References Cited

U.S. PATENT DOCUMENTS

| | | | |
|---|---|---|---|
| 6,193,659 B1* | 2/2001 | Ramamurthy | A61B 8/481 600/443 |
| 6,792,808 B1* | 9/2004 | Batzinger | G01N 29/11 73/602 |
| 2002/0049381 A1* | 4/2002 | Eck | A61B 8/00 600/447 |
| 2003/0055337 A1* | 3/2003 | Lin | B06B 1/0622 600/459 |
| 2005/0148877 A1* | 7/2005 | Guo | A61B 8/14 600/459 |
| 2010/0210949 A1* | 8/2010 | Habu | A61B 8/00 600/459 |
| 2011/0074244 A1 | 3/2011 | Osawa | |
| 2014/0211592 A1 | 7/2014 | Miyazawa | |
| 2014/0241112 A1* | 8/2014 | Kano | H01L 41/0475 367/7 |
| 2016/0266069 A1* | 9/2016 | Jenkins | G01N 29/043 |
| 2017/0027544 A1* | 2/2017 | Gemmeke | A61B 8/4494 |

FOREIGN PATENT DOCUMENTS

| | | |
|---|---|---|
| JP | 2011-160856 A | 8/2011 |
| JP | 2014-144100 A | 8/2014 |

* cited by examiner

ULTRASONIC DEVICE, ULTRASONIC MODULE, AND ULTRASONIC MEASUREMENT APPARATUS

BACKGROUND

1. Technical Field

The present invention relates to an ultrasonic device, an ultrasonic module, and an ultrasonic measurement apparatus.

2. Related Art

In the past, there has been known an ultrasonic diagnostic device (ultrasonic measurement apparatus) for transmitting/receiving an ultrasonic wave using an ultrasonic probe to thereby form an ultrasonic image (see, e.g., JP-A-2011-160856 (Document 1)).

In the device described in Document 1, the ultrasonic probe has a transmitting array and a receiving array. Among these arrays, the transmitting array is configured as a one-dimensional array having a plurality of fundamental resonators, which correspond to an ultrasonic wave as a fundamental wave, arranged in one direction (a scanning direction) in accordance with an arrangement condition corresponding to the fundamental wave. Further, the receiving array is configured as a one-dimensional array having a plurality of harmonic resonators, which correspond to an ultrasonic wave as a high-order harmonic wave with respect to the fundamental wave, arranged in the one direction described above in accordance with a predetermined arrangement condition corresponding to the order of a high-order harmonic wave. The transmitting array and the receiving array are arranged in parallel and close to each other.

Incidentally, in the ultrasonic array having the resonators described above, namely apertures, for transmitting/receiving the ultrasonic wave arranged to form the one-dimensionally array, by increasing the aperture size in a slicing direction perpendicular to the scanning direction, it is possible to improve the detection accuracy of the ultrasonic wave.

For example, in the case of converging the ultrasonic wave using the acoustic lens and so on, by increasing the size in the slicing direction of the aperture (transmitting aperture) for transmitting the ultrasonic wave, it is possible to converge the ultrasonic wave into a smaller area to thereby improve the resolution.

Further, by increasing the size in the slicing direction of the aperture (receiving aperture) for receiving the ultrasonic wave, it is possible to increase the receiving area of the ultrasonic wave. Thus, the receiving sensitivity of the ultrasonic wave in the receiving aperture can be improved.

However, in the device described in Document 1 mentioned above, the receiving array is disposed at a position approaching in the slicing direction to the transmitting array. Therefore, there is a problem that if the sizes of the transmitting aperture and the receiving aperture in the slicing direction are increased, the size of the whole of the ultrasonic array in the slicing direction increases, and thus, the ultrasonic probe grows in size. Therefore, it is difficult to achieve both of miniaturization of the ultrasonic probe and an improvement of the detection accuracy of the high-order harmonic wave with respect to the fundamental wave.

SUMMARY

An advantages of some aspects of the invention is to provide an ultrasonic device, an ultrasonic module, and an ultrasonic measurement apparatus each capable of achieving both of the miniaturization and the improvement of the detection accuracy of the high-order harmonic wave.

An ultrasonic device according to an application example of the invention includes a plurality of ultrasonic wave transmitting sections adapted to transmit an ultrasonic wave as a fundamental wave, and a plurality of ultrasonic wave receiving sections capable of receiving an N-th-order harmonic wave with respect to the fundamental wave, the plurality of ultrasonic wave transmitting sections and the plurality of ultrasonic wave receiving sections are arranged along a first direction, the plurality of ultrasonic wave receiving sections is arranged at first intervals corresponding to an order N of the N-th-order harmonic wave, the N ultrasonic wave transmitting sections constitute a single transmission channel, and are wired with each other, and the transmission channels are arranged at second intervals, each of which is N times as long as the first interval. As described in the embodiments, "N-th order" corresponds one of first-order, second-order, third-order, fourth-order, ... high-order . . . . Thus, "N" is a natural number.

Here, the first interval is the intervals of the ultrasonic wave receiving sections with which the N-th-order harmonic wave becomes to be able to be appropriately be received. The first interval is set, for example, so as to be equal to or smaller than the maximum interval corresponding to the wavelength (frequency) of the high-order harmonic wave with N-th order so that the high-order harmonic wave becomes to be able to be received with the desired accuracy.

In the ultrasonic device according to the application example, the ultrasonic wave transmitting sections and the ultrasonic wave receiving sections are arranged in a line. Further, the ultrasonic wave receiving sections are arranged at the first intervals corresponding to the order of the high-order harmonic wave. Further, by driving the corresponding number of ultrasonic wave transmitting sections to the order at the same time, these ultrasonic wave transmitting sections function as a single transmission channel, and the transmission channels are arranged at the second intervals each obtained by multiplying the first interval by the order of the high-order harmonic wave.

In such a configuration, since the interval between the transmission channels is the value obtained by multiplying the interval between the ultrasonic wave receiving sections (the reception channels) by the order, the high-order harmonic wave corresponding to the fundamental wave can accurately be detected.

Further, by arranging the ultrasonic wave transmitting sections and the ultrasonic wave receiving sections in a line, the ultrasonic device can be miniaturized compared to the configuration in which the transmission line formed of the ultrasonic wave transmitting sections and the reception line formed of the ultrasonic wave receiving sections are arranged in parallel to each other.

Further, in the case in which the ultrasonic device is formed with the same size as in the configuration in which the transmission line and the reception line described above are arranged in parallel to each other in the slicing direction, the dimension in the slicing direction of the transmitting aperture can be enlarged, and the resolution can be improved.

Further, in the application example, the ultrasonic wave transmitting sections and the ultrasonic wave receiving sections are arranged in a line. In such a configuration, the central position of the transmitting aperture and the central position of the receiving aperture can be made closer to each other compared to the configuration of arranging the transmission line and the reception line described above in parallel to each other. Therefore, it is possible to suppress the degradation of the resolution due to the central position of the transmitting aperture and the central position of the receiving aperture getting away from each other in a direction crossing the first direction of the ultrasonic wave transmitting sections and the ultrasonic wave receiving sections.

In the ultrasonic device according to the application example, it is preferable that the ultrasonic wave transmitting sections and the ultrasonic wave receiving sections are arranged alternately along the first direction.

In the application example with this configuration, the ultrasonic wave transmitting sections and the ultrasonic wave receiving sections are arranged alternately, the ultrasonic wave transmitting sections are arranged at predetermined intervals, and the ultrasonic wave receiving sections are arranged at predetermined intervals.

In such a configuration, the fundamental wave as a composite wave of the ultrasonic waves transmitted from the respective ultrasonic wave transmitting sections can more appropriately be transmitted compared to the case in which the interval between the ultrasonic wave transmitting sections varies in the first direction. For example, the fundamental wave having the wave front perpendicular to the propagation direction can more surely be transmitted.

In the ultrasonic device according to the application example, it is preferable that a dimension of the ultrasonic wave transmitting section in a second direction crossing the first direction of the ultrasonic wave transmitting section is larger than a dimension in the second direction of the ultrasonic wave receiving section.

In the application example with this configuration, in the second direction described above, the dimension of the ultrasonic wave transmitting section is larger than the dimension of the ultrasonic wave receiving section. In other words, in the second direction described above, the dimension of the ultrasonic wave receiving section is smaller than the dimension of the ultrasonic wave transmitting section.

Here, in the case of arranging the ultrasonic wave transmitting sections and the ultrasonic wave receiving sections in two lines, if the dimension of the ultrasonic wave transmitting section in the second direction is enlarged, the distance in the slicing direction between the central position of the ultrasonic wave transmitting section and the central position of the ultrasonic wave receiving section increases. Therefore, it results that the transmission direction of the ultrasonic wave is tilted toward the ultrasonic wave receiving section, and there is a possibility that the resolution is degraded.

In contrast, in the application example, since the ultrasonic wave transmitting sections and the ultrasonic wave receiving sections are arranged in a line, the dimension of the ultrasonic wave transmitting section in the second direction can be enlarged without changing the central positions in the slicing direction of the ultrasonic wave transmitting section and the ultrasonic wave receiving section. Therefore, the possibility of the degradation of the resolution described above does not exist, and moreover, the resolution can be improved by enlarging the size of the ultrasonic wave transmitting section as described above. Further, by decreasing the size of the ultrasonic wave receiving section, the reflected wave from the convergence region of the fundamental wave can more appropriately be received by the ultrasonic wave receiving sections, and thus, the resolution can be improved.

In the ultrasonic device according to the application example, it is preferable that the ultrasonic wave transmitting section overlaps an imaginary line, which passes through a central position of the ultrasonic wave receiving section in a second direction crossing the first direction, and is parallel to the first direction.

In the application example with this configuration, the imaginary line passing through the central position of each of the ultrasonic wave receiving sections (the receiving apertures) overlaps the ultrasonic wave transmitting section (the transmitting aperture). In other words, in the second direction, the center of the receiving aperture is located on the inner side of the both end parts of the transmitting aperture. Therefore, an amount of the shift between the centers of the transmitting aperture and the receiving aperture can be made smaller, and thus, the resolution can be improved compared to the case in which the center of the receiving aperture is located on the outer side of the receiving aperture in the second direction.

It should be noted that in the second direction, it is more preferable that the center of the transmitting aperture and the center of the receiving aperture coincide with each other. In this case, the propagation directions of the transmission wave and the reflected wave can be made roughly parallel to each other, and the resolution can further be improved.

In the ultrasonic device according to the application example, it is preferable that the ultrasonic wave receiving section is disposed at a position overlapping the ultrasonic wave transmitting section in a projection view along the first direction.

In the application example with this configuration, the ultrasonic wave receiving section (the receiving aperture) is disposed at a position overlapping the ultrasonic wave transmitting section (the transmitting aperture) in the projection view along the first direction. In other words, the ultrasonic wave receiving section is disposed so as to be included in the ultrasonic wave transmitting section in the projection view described above.

In such a configuration, it is possible to improve the resolution compared to the case in which at least a part of the ultrasonic wave receiving section is disposed at a position not overlapping the ultrasonic wave transmitting section in the projection view described above.

An ultrasonic module according to an application example of the invention includes an ultrasonic device provided with a plurality of ultrasonic wave transmitting sections adapted to transmit an ultrasonic wave as a fundamental wave, and a plurality of ultrasonic wave receiving sections capable of receiving an N-th-order harmonic wave with respect to the fundamental wave, and a circuit board on which the ultrasonic device is disposed, the plurality of ultrasonic wave transmitting sections and the plurality of ultrasonic wave receiving sections are arranged along a first direction, the plurality of ultrasonic wave receiving sections is arranged at first intervals corresponding to an order N of the N-th-order harmonic wave, the N ultrasonic wave transmitting sections constitute a single transmission channel, and are wired with each other, and the transmission channels are arranged at second intervals, each of which is N times as long as the first interval.

In the ultrasonic module according to the application example, similarly to the application example related to the ultrasonic device described above, among the ultrasonic wave transmitting sections and the ultrasonic wave receiving sections arranged in a line, the ultrasonic wave receiving sections are arranged at the first intervals corresponding to the order of the high-order harmonic wave with the N-th order, and the transmission channels each including a plurality of ultrasonic wave transmitting sections are arranged at the second intervals each obtained by multiplying the first interval by the order of the high-order harmonic wave.

In such a configuration, since the interval between the transmission channels is the value obtained by multiplying the interval between the reception channels by the order, the high-order harmonic wave can accurately be detected.

Further, since the ultrasonic wave transmitting sections and the ultrasonic wave receiving sections are arranged in a line, the ultrasonic device, and by extension, the ultrasonic module can be miniaturized compared to the configuration in which the transmission line and the reception line are arranged in parallel to each other.

Further, in the case in which the ultrasonic device is formed with the same size as in the configuration in which the transmission line and the reception line described above are arranged in parallel to each other in the slicing direction, the dimension in the slicing direction of the transmitting aperture can be enlarged, and the resolution can be improved.

Further, since the ultrasonic wave transmitting sections and the ultrasonic wave receiving sections are arranged in a line, the central position of the transmitting aperture and the central position of the receiving aperture can be made closer to each other, and thus, the degradation of the resolution can be suppressed compared to the configuration in which the transmission line and the reception line described above are arranged in parallel to each other.

An ultrasonic module according to an application example of the invention includes an ultrasonic device provided with a plurality of ultrasonic wave transmitting sections adapted to transmit an ultrasonic wave as a fundamental wave, and a plurality of ultrasonic wave receiving sections capable of receiving an N-th-order harmonic wave with respect to the fundamental wave, and a circuit board, on which the ultrasonic device is disposed, and which is provided with a selection section adapted to select the ultrasonic wave transmitting sections to which a same drive signal is input out of the plurality of ultrasonic wave transmitting sections, the plurality of ultrasonic wave transmitting sections and the plurality of ultrasonic wave receiving sections are arranged along a first direction, the plurality of ultrasonic wave receiving sections is arranged at first intervals corresponding to an order N of the N-th-order harmonic wave, and the selection section selects the ultrasonic wave transmitting sections so that an interval between transmission channels, each of which is constituted by driving the N ultrasonic wave transmitting sections at the same time, becomes a second interval N times as long as the first interval.

Similarly to the application example related to the ultrasonic device described above, in the ultrasonic module according to the application example, out of the ultrasonic wave transmitting sections and the ultrasonic wave receiving sections arranged in a line, the ultrasonic wave receiving sections are arranged at the first intervals corresponding to the order of the high-order harmonic wave. Further, the selection section selects the ultrasonic wave transmitting sections to be driven at the same time so that each of the intervals between the transmission channels each including the plurality of ultrasonic wave transmitting sections becomes the second interval obtained by multiplying the first interval by the order of the high-order harmonic wave.

In such a configuration, similarly to the ultrasonic device described above, since the interval between the transmission channels is the value obtained by multiplying the interval between the reception channels by the order, the high-order harmonic wave can accurately be detected.

Further, since the ultrasonic wave transmitting sections and the ultrasonic wave receiving sections are arranged in a line, the ultrasonic device, and by extension, the ultrasonic module can be miniaturized compared to the configuration in which the transmission line and the reception line are arranged in parallel to each other.

Further, in the case in which the ultrasonic device is formed with the same size as in the configuration in which the transmission line and the reception line described above are arranged in parallel to each other in the slicing direction, the dimension in the slicing direction of the transmitting aperture can be enlarged, and the resolution can be improved.

Further, since the ultrasonic wave transmitting sections and the ultrasonic wave receiving sections are arranged in a line, the central position of the transmitting aperture and the central position of the receiving aperture can be made closer to each other, and thus, the degradation of the resolution can be suppressed compared to the configuration in which the transmission line and the reception line described above are arranged in parallel to each other.

Further, the application example is configured such that the selection section provided to the circuit board can select the ultrasonic wave transmitting sections to be driven at the same time. Thus, it is possible to, for example, individually drive the ultrasonic wave transmitting sections to set the fundamental wave as the reception object, and the convenience of the ultrasonic measurement apparatus can be enhanced.

An ultrasonic measurement apparatus according to an application example of the invention includes an ultrasonic device provided with a plurality of ultrasonic wave transmitting sections adapted to transmit an ultrasonic wave as a fundamental wave, and a plurality of ultrasonic wave receiving sections capable of receiving an N-th-order harmonic wave with respect to the fundamental wave, and a control section adapted to control the ultrasonic device, the plurality of ultrasonic wave transmitting sections and the plurality of ultrasonic wave receiving sections are arranged along a first direction, the plurality of ultrasonic wave receiving sections is arranged at first intervals corresponding to an order N of the N-th-order harmonic wave, the N ultrasonic wave transmitting sections constitute a single transmission channel, and are wired with each other, and the transmission channels are arranged at second intervals, each of which is N times as long as the first interval.

In the ultrasonic measurement apparatus according to the application example, similarly to the application examples related to the ultrasonic device and the ultrasonic module described above, among the ultrasonic wave transmitting sections and the ultrasonic wave receiving sections arranged in a line, the ultrasonic wave receiving sections are arranged at the first intervals corresponding to the order of the high-order harmonic wave, and the transmission channels each including a plurality of ultrasonic wave transmitting sections are arranged at the second intervals each obtained by multiplying the first interval by the order of the high-order harmonic wave.

In such a configuration, since the interval between the transmission channels is the value obtained by multiplying the interval between the reception channels by the order, the high-order harmonic wave can accurately be detected.

Further, since the ultrasonic wave transmitting sections and the ultrasonic wave receiving sections are arranged in a line, the ultrasonic device, and by extension, the ultrasonic measurement apparatus can be miniaturized compared to the configuration in which the transmission line and the reception line are arranged in parallel to each other.

Further, in the case in which the ultrasonic device is formed with the same size as in the configuration in which the transmission line and the reception line described above are arranged in parallel to each other in the slicing direction, the dimension in the slicing direction of the transmitting aperture can be enlarged, and the resolution can be improved.

Further, since the ultrasonic wave transmitting sections and the ultrasonic wave receiving sections are arranged in a line, the central position of the transmitting aperture and the central position of the receiving aperture can be made closer to each other, and thus, the degradation of the resolution can be suppressed compared to the configuration in which the transmission line and the reception line described above are arranged in parallel to each other.

An ultrasonic measurement apparatus according to an application example of the invention includes an ultrasonic device provided with a plurality of ultrasonic wave transmitting sections adapted to transmit an ultrasonic wave as a fundamental wave, and a plurality of ultrasonic wave receiving sections capable of receiving an N-th-order harmonic wave with respect to the fundamental wave, a selection section adapted to select the ultrasonic wave transmitting sections to which a same drive signal is input, and a control section adapted to control the ultrasonic device and the selection section, the plurality of ultrasonic wave transmitting sections and the plurality of ultrasonic wave receiving sections are arranged along a first direction, the plurality of ultrasonic wave receiving sections is arranged at first intervals corresponding to an order N of the N-th-order harmonic wave, the selection section selects the ultrasonic wave transmitting sections based on control by the control section so that an interval between transmission channels, each of which is constituted by driving the N ultrasonic wave receiving sections at the same time, becomes a second interval N times as long as the first interval.

Similarly to the application examples related to the ultrasonic device and the ultrasonic module described above, in the ultrasonic measurement apparatus according to the application example, out of the ultrasonic wave transmitting sections and the ultrasonic wave receiving sections arranged in a line, the ultrasonic wave receiving sections are arranged at the first intervals corresponding to the order of the high-order harmonic wave. Further, the selection section selects the ultrasonic wave transmitting sections to be driven at the same time so that each of the intervals between the transmission channels each including the plurality of ultrasonic wave transmitting sections becomes the second interval obtained by multiplying the first interval by the order of the high-order harmonic wave.

In such a configuration, since the interval between the transmission channels is the value obtained by multiplying the interval between the reception channels by the order, the high-order harmonic wave can accurately be detected.

Further, since the ultrasonic wave transmitting sections and the ultrasonic wave receiving sections are arranged in a line, the ultrasonic device, and by extension, the ultrasonic measurement apparatus can be miniaturized compared to the configuration in which the transmission line and the reception line are arranged in parallel to each other.

Further, in the case in which the ultrasonic device is formed with the same size as in the configuration in which the transmission line and the reception line described above are arranged in parallel to each other in the slicing direction, the dimension in the slicing direction of the transmitting aperture can be enlarged, and the resolution can be improved.

Further, since the ultrasonic wave transmitting sections and the ultrasonic wave receiving sections are arranged in a line, the central position of the transmitting aperture and the central position of the receiving aperture can be made closer to each other, and thus, the degradation of the resolution can be suppressed compared to the configuration in which the transmission line and the reception line described above are arranged in parallel to each other.

Further, the application example is configured such that the selection section provided to the circuit board can select the ultrasonic wave transmitting sections to be driven at the same time. Thus, it is possible to, for example, individually drive the ultrasonic wave transmitting sections to set the fundamental wave as the reception object, and the convenience of the ultrasonic measurement apparatus can be enhanced.

In the ultrasonic measurement apparatus according to the application example, it is preferable that the plurality of ultrasonic wave receiving sections is capable of receiving a plurality of high-order harmonic waves with respective orders, and is arranged at the first intervals corresponding to highest one of the orders, and the selection section selects the ultrasonic wave transmitting sections so that the second interval becomes a product of the order of the high-order harmonic wave as a reception object and the first interval.

In the application example, the plurality of high-order harmonic waves with respective orders is set as the reception object, and the first intervals as the arrangement intervals of the ultrasonic wave receiving sections are each an interval corresponding to the highest order. Further, the selection section selects the ultrasonic wave transmitting sections in accordance with the order of the high-order harmonic wave as the reception object, and then makes these be driven at the same time.

In such a configuration, since the ultrasonic wave receiving sections are arranged at the intervals corresponding to the highest order of the plurality of orders, when setting the plurality of orders as the detection object, the high-order harmonic wave with the order lower than the highest order, and the high-order harmonic wave with the highest order and lower in strength than the fundamental wave can more surely be detected.

Further, since the selection section selects the ultrasonic wave transmitting sections to the object of the simultaneous drive in accordance with the order of the reception object, the intervals of the transmission channels can be set in accordance with the order of the reception object. Therefore, even in the case of detecting the plurality of high-order harmonic waves with the respective orders, the detection accuracy of the high-order harmonic waves with the respective orders can be improved.

In the ultrasonic measurement apparatus according to the application example, it is preferable that the ultrasonic wave receiving section is provided with receiving elements corresponding respectively to the orders as the reception object.

Here, the high-order harmonic wave has the frequency obtained by multiplying the frequency of the fundamental wave by the order in accordance with the order. In the application example, the receiving element corresponding to the order of the reception object means, for example, a receiving element having desired sensitivity corresponding to the measurement accuracy with respect to the harmonic wave having the frequency corresponding to the order.

In the application example with this configuration, the ultrasonic wave receiving sections are each provided with the receiving elements corresponding respectively to the plurality of orders. Thus, even in the case of setting the plurality of high-order harmonic waves with the respective orders as the reception object, the detection accuracy of the harmonic waves with the respective orders can be improved.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

An ultrasonic measurement apparatus as an electronic apparatus of a first embodiment according to the invention will hereinafter be described based on the accompanying drawings.

Configuration of Ultrasonic Measurement Apparatus

Figure 1:
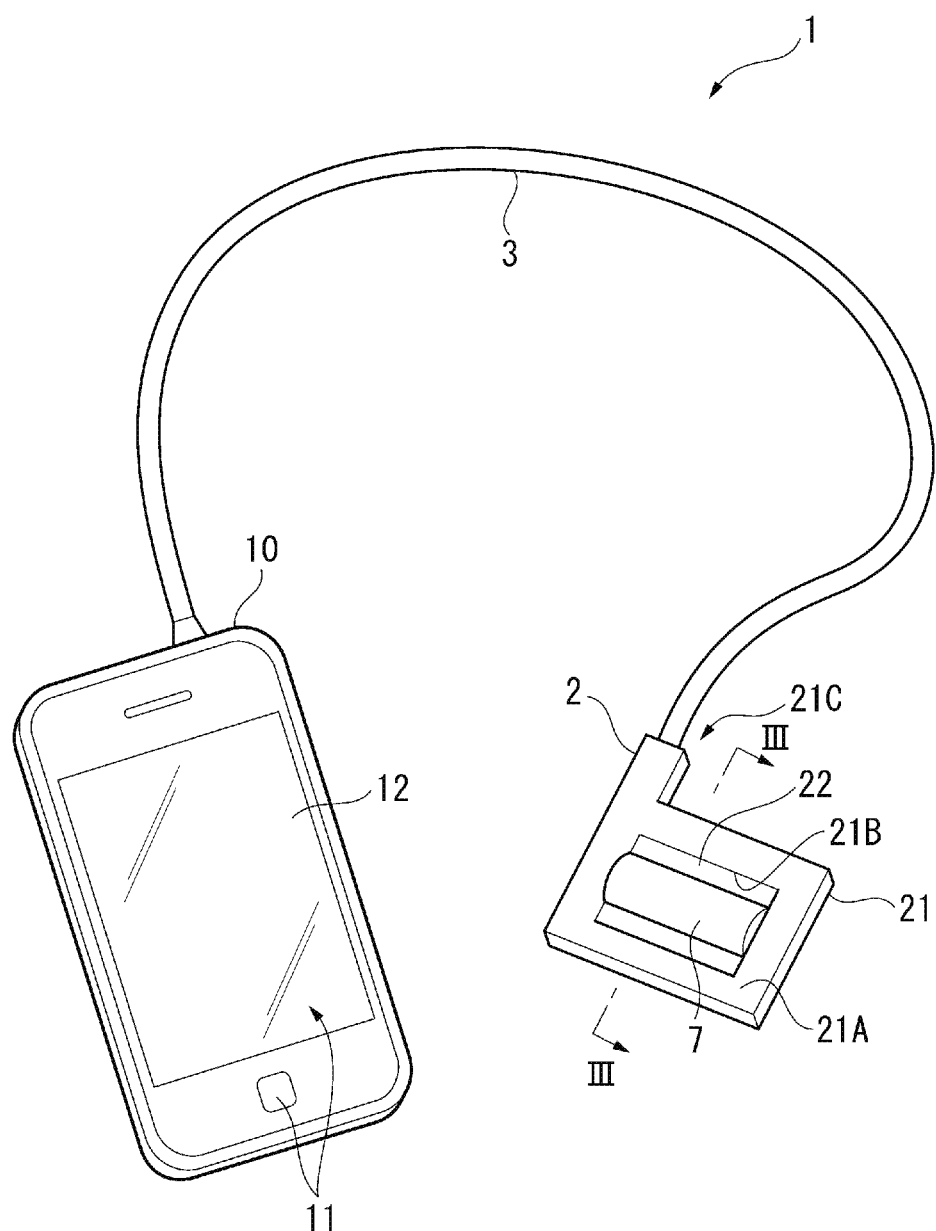
FIG. 1 is a perspective view showing a schematic configuration of an ultrasonic measurement apparatus according to a first embodiment of the invention.
Figure 2:
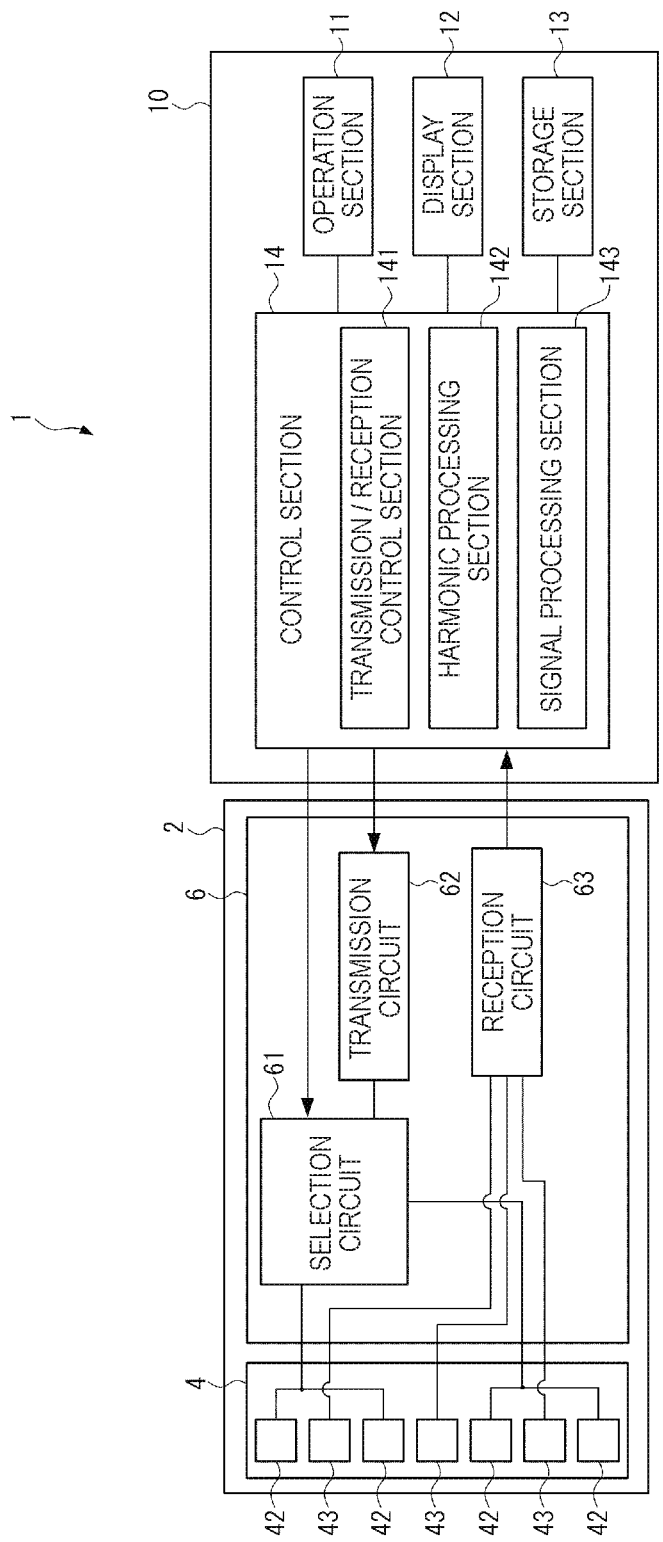
FIG. 2 is a block diagram showing a schematic configuration of the ultrasonic measurement apparatus according to the first embodiment.

FIG. 1 is a perspective view showing a schematic configuration of the ultrasonic measurement apparatus 1 according to the present embodiment. FIG. 2 is a block diagram showing a schematic configuration of the ultrasonic measurement apparatus 1.

As shown in FIG. 1, the ultrasonic measurement apparatus 1 according to the present embodiment is provided with an ultrasonic probe 2, and a control device 10 electrically connected to the ultrasonic probe 2 via a cable 3.

The ultrasonic measurement apparatus 1 transmits an ultrasonic wave from the ultrasonic probe 2 to the inside of a living body (e.g., a human body) with the ultrasonic probe 2 having contact with a surface of the living body. Further, the ultrasonic measurement apparatus 1 receives a high-order harmonic wave with respect to the fundamental wave among the ultrasonic wave reflected by a part in the living body using the ultrasonic probe 2, and then, for example, obtains an internal tomographic image in the living body, and measures the state (e.g., blood flow) of the part in the living body based on the received signal.

Configuration of Ultrasonic Probe

Figure 3:
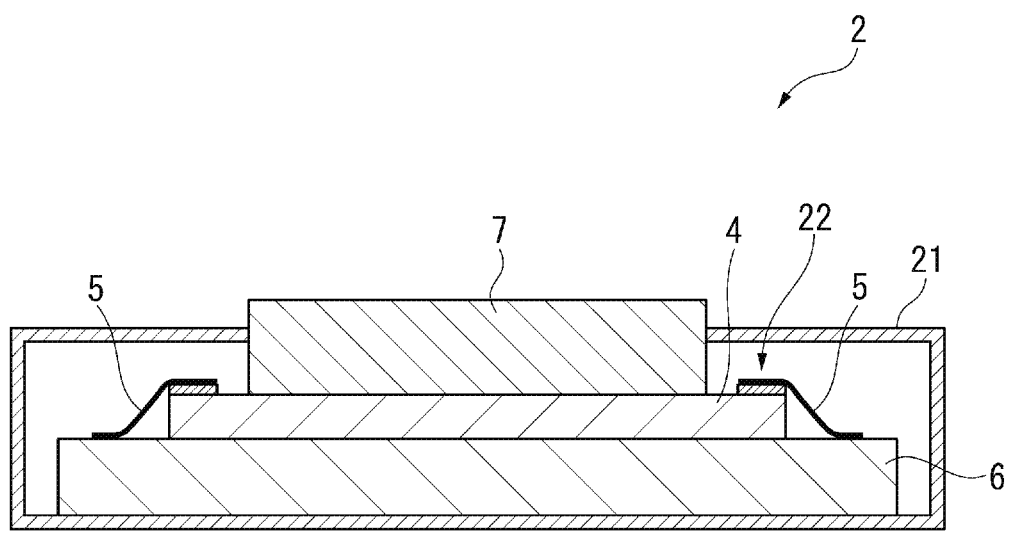
FIG. 3 is a cross-sectional view showing a schematic configuration of an ultrasonic probe according to the first embodiment.

FIG. 3 is a cross-sectional view of the ultrasonic probe 2 cut along the line III-III shown in FIG. 1, and showing a schematic configuration of the ultrasonic probe 2.

The ultrasonic probe 2 is provided with a housing 21 and an ultrasonic sensor 22.

Configuration of Housing

As shown in FIG. 1, the housing 21 is formed to have a box-like shape having a rectangular planar shape, and supports the ultrasonic sensor 22. One surface (a sensor surface 21A) perpendicular to the thickness direction of the housing 21 is provided with a sensor window 21B, and a part (an acoustic lens 7 described later) of the ultrasonic sensor 22 is exposed. Further, in a part (a side surface in the example shown in FIG. 1) of the housing 21, there is disposed a through hole 21C for the cable 3, and the cable 3 is inserted into the housing 21. Although not shown in the drawings, the cable 3 is connected to the ultrasonic sensor 22 (via a circuit board 6 described later) in the inside of the housing 21. Further, the gap between the cable 3 and the through hole 21C is filled with, for example, a resin material to thereby ensure the waterproof property.

It should be noted that although in the present embodiment, there is shown a configuration example in which the ultrasonic probe 2 and the control device 10 are connected to each other using the cable 3, the configuration is not limited to this example, and it is also possible to, for example, connect the ultrasonic probe 2 and the control device 10 to each other with wireless communication, or dispose a variety of constituents of the control device 10 inside the ultrasonic probe 2.

Configuration of Ultrasonic Sensor

The ultrasonic sensor 22 corresponds to the ultrasonic module according to the invention, and is provided with an ultrasonic device 4, a flexible board 5, the circuit board 6, and the acoustic lens 7 as shown in FIG. 3. Although described later, the circuit board 6 is provided with a driver circuit for controlling the ultrasonic device 4 and so on, and the ultrasonic device 4 is electrically connected to the circuit board 6 via the flexible board 5. On the ultrasonic wave transmission/reception side surface of the ultrasonic device 4, there is disposed the acoustic lens 7. The ultrasonic sensor 22 is housed in the housing 21 so that the acoustic lens 7 is exposed, transmits the ultrasonic wave from the exposed part to an object, and then receives a reflected wave from the object.

Configuration of Acoustic Lens

The acoustic lens 7 efficiently propagate the ultrasonic wave, which has been emitted from the ultrasonic device 4, to the living body as the measurement object, and further propagate the ultrasonic wave, which has been reflected in the living body, to the ultrasonic device 4 with efficiency. The acoustic lens 7 is disposed along the surface with which the ultrasonic device 4 transmits and receives the ultrasonic wave. It should be noted that although not shown in the drawings, between the ultrasonic device 4 and the acoustic lens 7, there is disposed an acoustic matching layer. The acoustic lens 7 and the acoustic matching layer are set to have an acoustic impedance intermediate between the acoustic impedance of the ultrasonic elements 40 (transmitting element 421 and receiving element 431) of an element substrate 41 and the acoustic impedance of the living body.

Configuration of Ultrasonic Device

Figure 4:
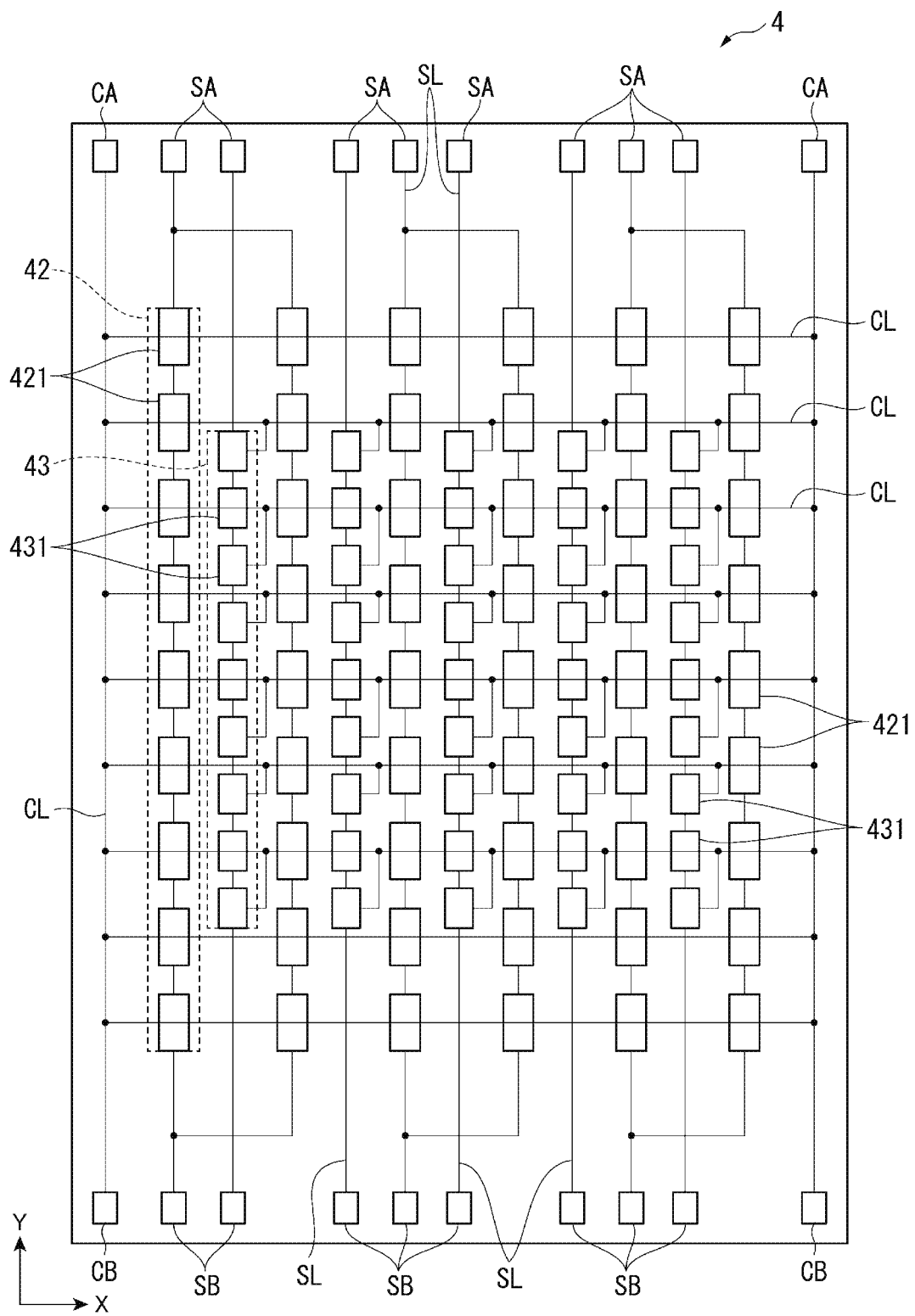
FIG. 4 is a plan view showing the schematic configuration of an ultrasonic device according to the first embodiment.

FIG. 4 is a plan view of the ultrasonic device 4 viewed from the acoustic lens 7 side, and showing a schematic configuration of the ultrasonic device 4.

In the following description, the scanning direction (a first direction) of the ultrasonic device 4 having a one-dimensional array structure as described later is defined as an X direction, and the slicing direction (a second direction) perpendicular to the scanning direction is defined as a Y direction.

The ultrasonic device 4 is provided with ultrasonic wave transmitting sections 42, ultrasonic wave receiving sections 43, signal electrode lines SL, common electrode lines CL, first signal terminals SA, second signal terminals SB, first common terminals CA, and second common terminals CB, and these constituents are disposed on the element substrate 41.

Among these constituents, the ultrasonic wave transmitting sections 42 each have a plurality of transmitting elements 421 as ultrasonic elements for transmission, and are each constituted by these transmitting elements 421 arranged along the Y direction. Further, the ultrasonic wave receiving sections 43 each have a plurality of receiving elements 431 as ultrasonic elements for reception, and are each constituted by these receiving elements 431 arranged along the Y direction.

It should be noted that in the ultrasonic device 4 according to the present embodiment, the ultrasonic wave transmitting sections 42 and the ultrasonic wave receiving sections 43 are alternately arranged in the X direction, a pair of ultrasonic wave transmitting sections 42 adjacent to each other in the X direction function as a single transmission channel, and each of the ultrasonic wave receiving sections 43 functions as a single reception channel. Further, the second-order harmonic wave corresponding to the fundamental wave transmitted from each of the transmission channels is received by each of the reception channels.

Configuration of Element Substrate

Figure 5A:
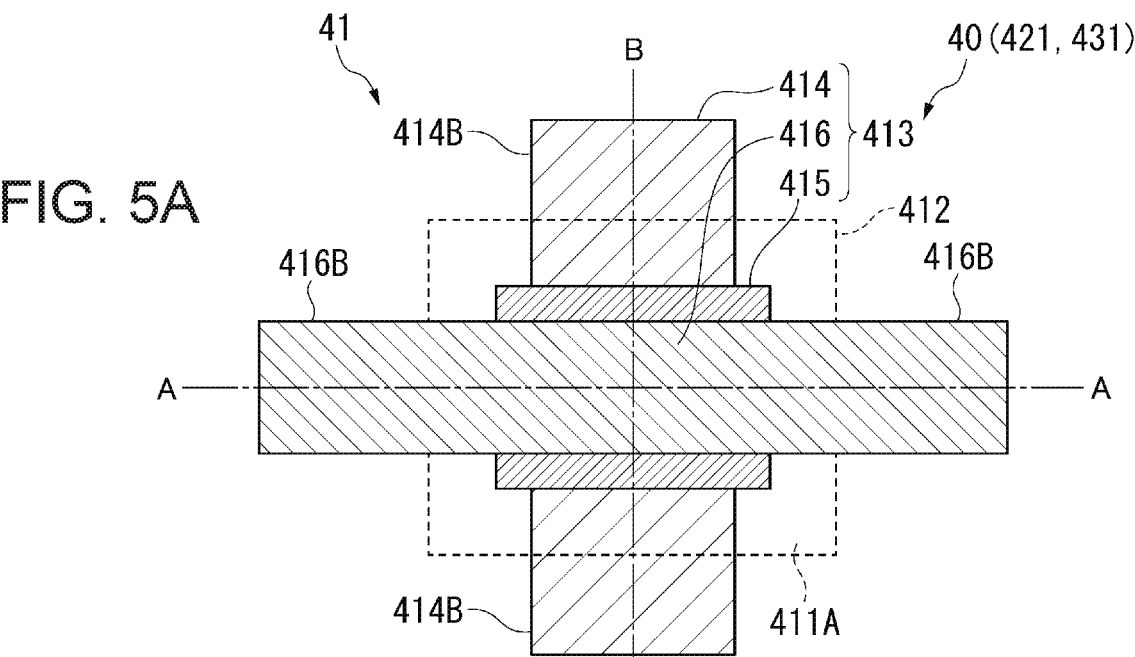
FIGS. 5A through 5C are diagrams schematically showing a configuration of an ultrasonic element according to the first embodiment.
Figure 5B:
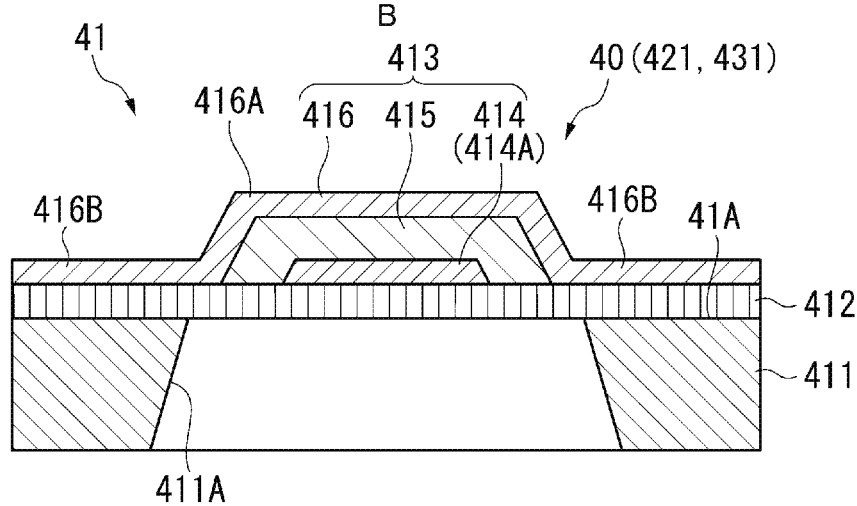
Figure 5C:
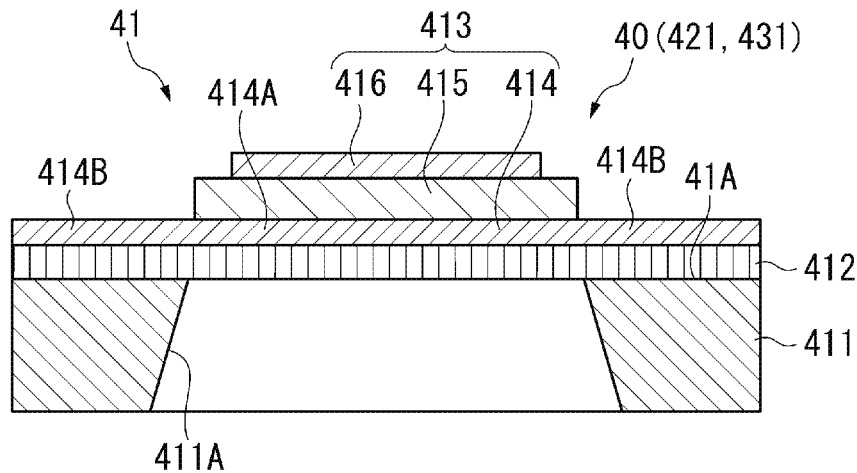

FIGS. 5A through 5C show an example of a configuration of the element substrate 41 and the ultrasonic element 40. FIG. 5A is a plan view of the transmitting element 421, FIG. 5B is a cross-sectional view showing a cross-sectional surface along the line A-A shown in FIG. 5A, and FIG. 5C is a cross-sectional view showing a cross-sectional surface along the line B-B shown in FIG. 5A.

As shown in FIGS. 5A through 5C, the element substrate 41 is provided with a substrate main body part 411, a vibrating film 412 stacked on the substrate main body part 411, and piezoelectric elements 413 stacked on the vibrating film 412. Here, the vibrating film 412 and the piezoelectric element 413 constitute the ultrasonic element 40 (the transmitting element 421 and the receiving element 431).

The substrate main body part 411 is a semiconductor substrate made of, for example, Si. Inside the array region of the substrate main body part 411, there are disposed aperture parts 411A corresponding respectively to the ultrasonic elements. Further, the aperture parts 411A are closed by the vibrating film 412 disposed on the rear surface 41A side of the substrate main body part 411.

The vibrating film 412 is formed of, for example, $SiO_2$ or a laminated body of $SiO_2$ and $ZrO_2$, and is disposed so as to cover the entire area on the rear surface 41A side of the substrate main body part 411. The thickness dimension of the vibrating film 412 becomes sufficiently small one with respect to the substrate main body part 411. In the case of forming the substrate main body part 411 using Si and forming the vibrating film 412 using $SiO_2$, by performing an oxidation treatment on, for example, the surface on the rear surface 41A side of the substrate main body part 411, it becomes possible to easily form the vibrating film 412 having a desired thickness dimension. Further, in this case, by performing an etching treatment on the substrate main body part 411 using the vibrating film 412 made of $SiO_2$ as an etching stopper, it is possible to easily form the aperture parts 411A.

Configuration of Ultrasonic Wave Transmitting Sections

As described above, the ultrasonic wave transmitting sections 42 are each provided with the plurality of transmitting elements 421. As shown in FIGS. 5A through 5C, the transmitting elements 421 are each configured including the vibrating film 412 and the piezoelectric element 413.

The piezoelectric element 413 is a laminated body of a lower-part electrode 414, a piezoelectric film 415, and an upper-part electrode 416, and is disposed on the vibrating film 412 closing each of the aperture parts 411A as shown in FIGS. 5A through 5C.

In such a transmitting element 421, by applying a rectangular-wave voltage having a predetermined frequency between the lower-part electrode 414 and the upper-part electrode 416, it is possible to vibrate the vibrating film 412 in an aperture region of each of the aperture parts 411A to transmit the ultrasonic wave. Here, the vibrating film. 412 (the aperture size of the aperture part 411A) of the transmitting element 421 has a dimension corresponding to the fundamental wave corresponding to the second-order harmonic wave of the reception object described above. Thus, it is possible to transmit the fundamental wave with a desired efficiency by the transmitting element 421.

The lower-part electrode 414 has a lower-part electrode main body 414A and a lower-part electrode line 414B, and is formed to have a shape of a straight line along the Y direction so as to straddle two or more transmitting elements 421. Therefore, in the transmitting elements 421 arranged in the Y direction, the lower-part electrodes 414 become in the same potential. The lower-part electrode 414 is connected to corresponding one of the first signal terminals SA disposed in an outer peripheral part on the +Y side of the element substrate 41 and corresponding one of the second signal terminals SB disposed in an outer peripheral part on the −Y side of the element substrate 41 with the signal electrode lines SL. To the lower-part electrodes 414, there are applied drive voltages via the respective signal terminals SA, SB (see FIG. 4).

In the present embodiment, the two ultrasonic wave transmitting sections 42 arranged in the Y direction are treated as a pair to constitute a single transmission channel. Specifically, as shown in FIG. 4, the two ultrasonic wave transmitting sections 42 adjacent to each other are connected to the same signal terminals SA, SB.

The piezoelectric film 415 is formed of a thin film made of lead zirconate titanate (PZT) or the like, and is configured so as to cover at least the lower-part electrode 414.

The upper-part electrode 416 has an upper-part electrode main body 416A (see FIGS. 5A through 5C) and an upper-part electrode line 416B (see FIGS. 5A through 5C). The upper-part electrode 416 is connected to the first common terminals CA and the second common terminals CB (see FIG. 4) with the common electrode lines CL, and a common voltage is applied to the upper-part electrode 416.

Configuration of Ultrasonic Wave Receiving Sections

As described above, the ultrasonic wave receiving sections 43 are each provided with the plurality of receiving elements 431 arranged along the Y direction. The plurality of ultrasonic wave receiving sections 43 is arranged in the X direction. The ultrasonic wave receiving sections 43 basically have roughly the same configuration except the point that the receiving elements 431 as the ultrasonic elements 40 are provided, and the point that the dimension in the Y direction (the slicing direction) is smaller than that of the ultrasonic wave transmitting sections 42.

In other words, the receiving elements 431 each have basically similar configuration to that of each of the transmitting elements 421, and are each configured including the vibrating film 412 and the piezoelectric element 413. In the receiving element 431, in order to efficiently receive the second-order harmonic wave (a high-order harmonic wave with the central frequency of 2f0 in the case of assuming the central frequency of the fundamental wave as f0) corresponding to the fundamental wave emitted from the transmitting element 421, the dimension of the vibrating film 412 is set to the dimension corresponding to the second-order harmonic wave.

The ultrasonic wave receiving sections 43 are respectively connected to the signal terminals SA, SB different from each other with the signal electrode lines SL. Further, the ultrasonic wave receiving sections 43 are connected to the common terminals CA, CB with the common electrode lines CL (see FIG. 4). In other words, each of the ultrasonic wave receiving sections 43 arranged in the X direction at regular intervals functions as a single reception channel.

Figure 6:
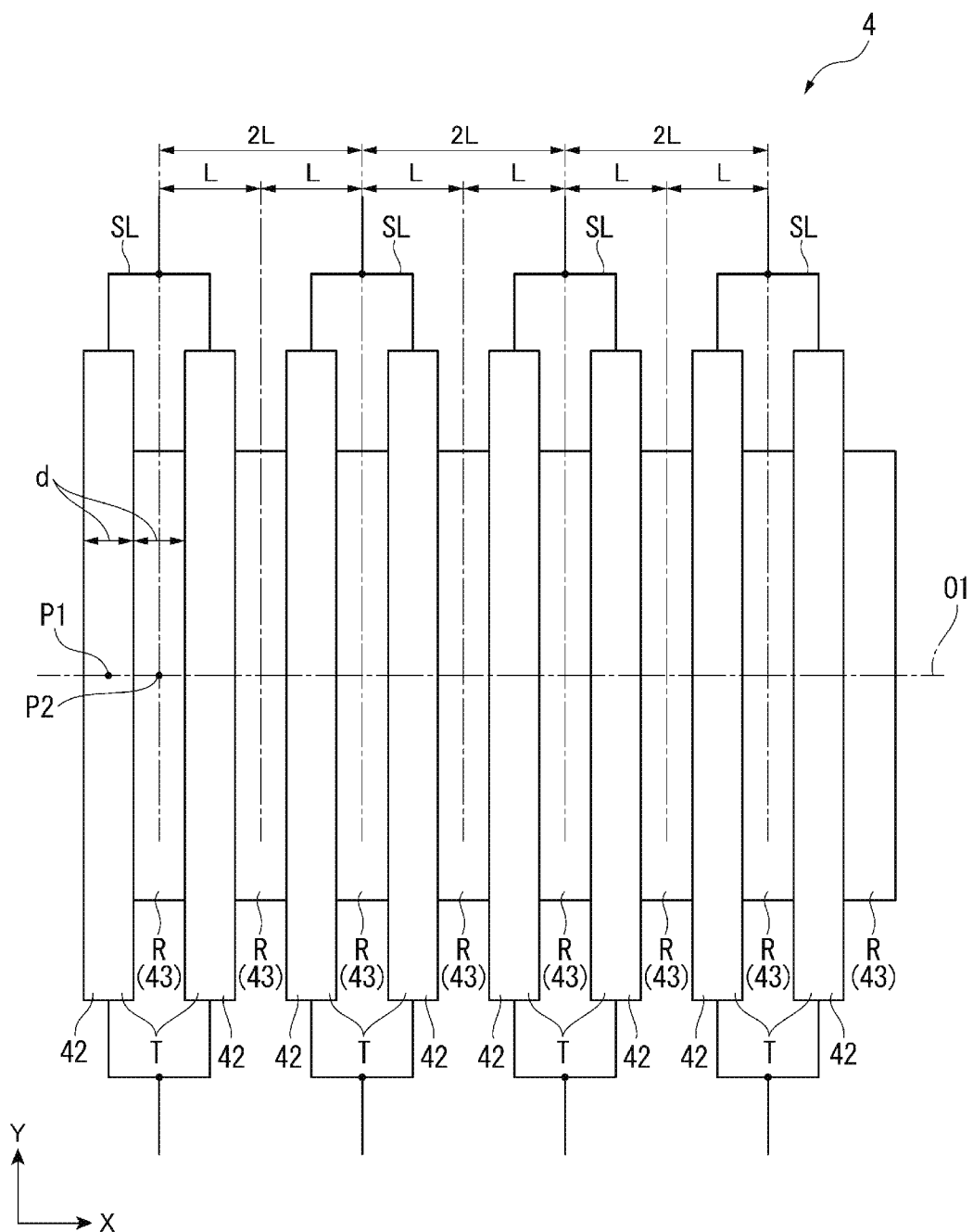
FIG. 6 is a diagram schematically showing an ultrasonic device according to the first embodiment.

Arrangement of Ultrasonic Wave Transmitting Sections and Ultrasonic Wave Receiving Sections FIG. 6 is a diagram schematically showing a general configuration of the ultrasonic device 4 equipped with the ultrasonic wave transmitting sections 42 and the ultrasonic wave receiving sections 43. It should be noted that FIG. 6 only shows the signal electrode lines SL in the ultrasonic wave transmitting sections 42 among the signal electrode lines SL and the common electrode lines CL.

As shown in FIG. 6, the ultrasonic wave transmitting sections 42 and the ultrasonic wave receiving sections 43 are arranged alternately.

The ultrasonic wave transmitting sections 42 and the ultrasonic wave receiving sections 43 are each arranged at predetermined intervals.

The ultrasonic wave receiving sections 43 each function as a single reception channel R. The ultrasonic wave receiving sections 43, namely the reception channels R, are arranged at intervals of L (reception pitch). Here, the reception pitch L is set in accordance with the second-order harmonic wave corresponding to the fundamental wave. It should be noted that the reception pitch L is set to a dimension equal to or smaller than the maximum distance Lmax with which the second-order harmonic wave corresponding to the fundamental wave transmitted from the ultrasonic wave transmitting sections 42 can be obtained with desired accuracy.

Here, as described above, the two ultrasonic wave transmitting sections 42 adjacent to each other in the X direction out of the plurality of ultrasonic wave transmitting sections 42 are wired with the signal electrode lines SL to constitute a single transmission channel T. The transmission channels T are arranged at predetermined intervals of 2L. In other words, the plurality of transmission channels T is arranged along the X direction at the intervals of 2L (transmission pitch 2L). As described above, in the present embodiment, the transmission pitch is set to be twice as large as the reception pitch. Thus, the second-order harmonic wave corresponding to the fundamental wave can accurately be received compared to the case in which the transmission pitch and the reception pitch are the same as each other.

Figure 7:
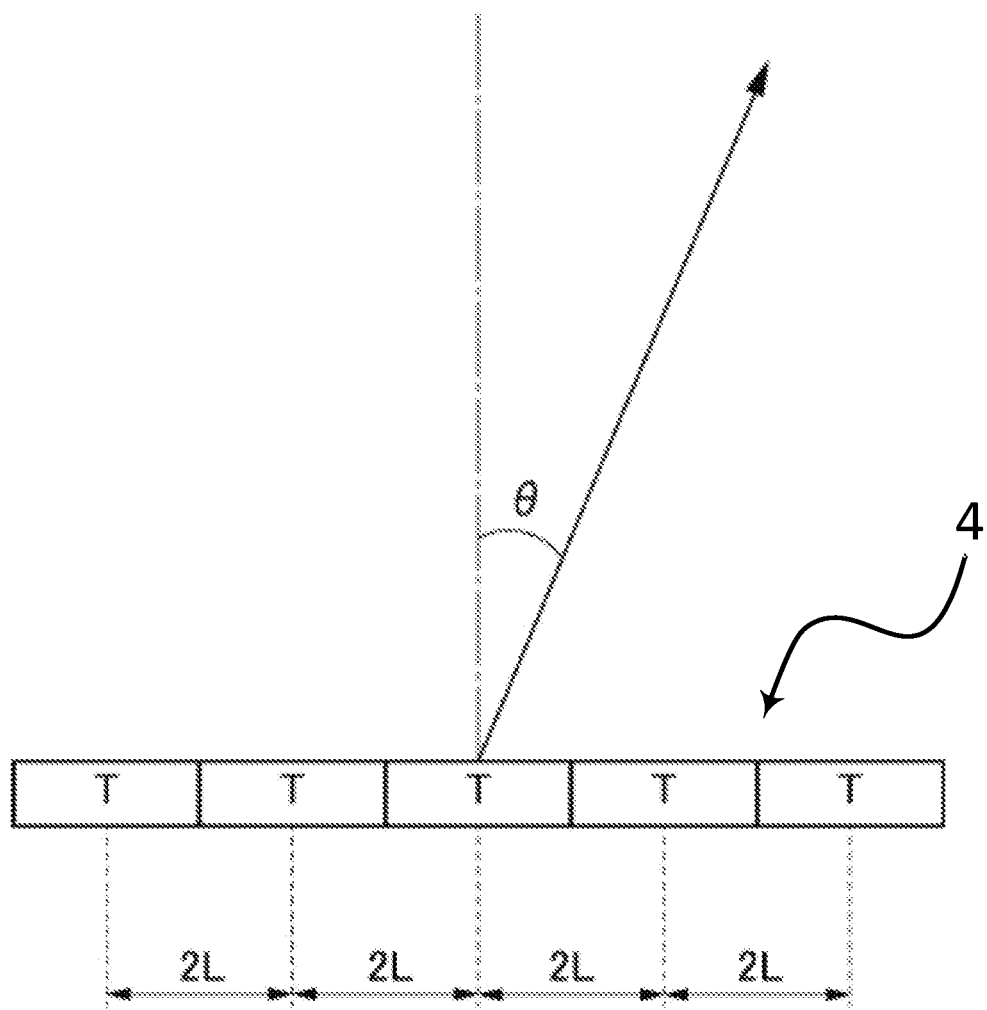
FIG. 7 is a diagram schematically showing the ultrasonic device according to the first embodiment.

FIG. 7 is a diagram schematically showing the ultrasonic device 4 according to the first embodiment. Specifically FIG. 7 shows the condition in which the fundamental wave is transmitted from the transmission channel T of the ultrasonic device 4.

In the case in which the transmission timing of the fundamental wave (the wavelength λ) from each of the transmission channels T is delayed in sequence to set the range of a predetermined scanning angle θ as the scanning object, the transmission pitch 2L is set so as to fulfill the grating lobe condition expressed by Formula (1) described below. By setting the transmission pitch 2L in such a manner as described above, occurrence of the grating lobe can be suppressed as long as the scanning angle is within the range of θ.

It should be noted that if it is assumed that the ultrasonic wave transmitting sections 42 and the ultrasonic wave receiving section 43 are arranged at regular intervals, and the dimension in the X direction of the ultrasonic wave transmitting section 42, namely the transmitting aperture, is d, in the present embodiment, the dimension in the X direction of the ultrasonic wave receiving sections 43, namely the receiving aperture, is also d, and the relationship expressed by Formula (2) described below exists between L and d, and d is set so as to fulfill Formula (3) below.

$$2L < \lambda/(1+\sin\theta) \quad (1)$$

$$2L = 4d \quad (2)$$

$$d < \lambda/4(1+\sin\theta) \quad (3)$$

Going back to FIG. 6, in the ultrasonic device 4, the ultrasonic wave transmitting sections 42 and the ultrasonic wave receiving sections 43 are disposed so that the central position P1 of the transmitting aperture and the central position P2 of the receiving aperture are located on an imaginary line O1 parallel to the Y axis. In such a configuration, it is possible to receive an ultrasonic wave, which is transmitted along a surface perpendicular to the ultrasonic array, then reflected, and then propagates along that surface. Therefore, it is possible to improve the resolution compared to the configuration in which the respective centers of the transmitting apertures and the receiving apertures are disposed so as to be shifted from each other in the Y direction, and the reflected wave, which has propagated at a different angle from that of the ultrasonic wave having been transmitted, is received.

Further, since the central positions P1, P2 coincide with each other in a projection view along the scanning direction (the X direction), the dimension (the dimension of a receiving slicing aperture) in the Y direction of the ultrasonic wave receiving section 43 can be made smaller, and thus, the resolution can be improved.

It should be noted that in the present embodiment, the dimension (the dimension of the transmitting slicing aperture) in the Y direction of the ultrasonic wave transmitting section 42 is smaller than the dimension (the dimension of the receiving slicing aperture) of the ultrasonic wave receiving section 43. Further, the ultrasonic wave transmitting section 42 is disposed at a position overlapping the inside of the ultrasonic wave receiving section 43. Thus, an improvement in resolution can be achieved.

Configuration of Circuit Board

The circuit board 6 is provided with a drive signal terminal (not shown) and a common terminal (not shown), and the ultrasonic device 4 is connected to the circuit board 6 with the flexible board 5. Further, the circuit board 6 is connected to the control device 10 via the cable 3.

The circuit board 6 is provided with a driver circuit for driving the ultrasonic device 4, and so on. Specifically, as shown in FIG. 2, the circuit board 6 is provided with a selection circuit 61, a transmission circuit 62, and a reception circuit 63.

The selection circuit 61 corresponds to a selection section according to the invention, and selects the transmission channel T (the ultrasonic wave transmitting section 42) to be connected to the transmission circuit 62 based on the control by the control device 10.

The transmission circuit 62 outputs a transmission signal, which represents the fact that the ultrasonic device 4 is made to transmit the ultrasonic wave via the selection circuit 61 when switching to the transmission connection is made due to the control by the control device 10. It should be noted that the transmitting elements 421 included in the ultrasonic wave transmitting section 42 selected by the selection circuit 61 is driven in accordance with the output of the transmission signal, and transmits an ultrasonic wave.

The reception circuit 63 outputs a reception signal, which has been input from the ultrasonic sensor 22, to the control device 10. The reception circuit 63 is configured including, for example, a low-noise amplifier circuit, a voltage-controlled attenuator, a programmable-gain amplifier, a low-pass filter, an A/D converter, and a phasing addition circuit, and performs a variety of signal processing such as conversion of the reception signal into a digital signal, elimination of a noise component, amplification to a desired signal level, and a phasing addition processing on each of the reception channels, and then outputs the reception signal thus processed to the control device 10.

Configuration of Control Device

As shown in FIG. 2, the control device 10 is configured including, for example, an operation section 11, a display section 12, a storage section 13, and a control section 14. As the control device 10, there can be used a terminal device such as a tablet terminal, a smartphone, or a personal computer, and the control device 10 can also be a dedicated terminal device for operating the ultrasonic probe 2.

The operation section 11 is a user interface (UI) for the user to operate the ultrasonic measurement apparatus 1, and can be formed of, for example, a touch panel or operation buttons disposed on the display section 12, a keyboard, or a mouse.

The display section 12 is formed of, for example, a liquid crystal display, and displays an image.

The storage section 13 stores a variety of programs and a variety of data for controlling the ultrasonic measurement apparatus 1.

The control section 14 is formed of an arithmetic circuit such as a central processing unit (CPU), a processing circuit for performing each of the processes described later, and a storage circuit such as a memory. Further, the control section 14 reads and executes the variety of programs stored in the storage section 13 to thereby function as a transmission/reception control section 141, a harmonic processing section 142, and a signal processing section 143.

The transmission/reception control section 141 performs control of making the selection circuit 61 select the transmission channel T to be the driving object. Further, the transmission/reception control section 141 performs control of a generation and output process of the transmission signal on the transmission circuit 62. Further, the transmission/reception control section 141 performs control of frequency setting, gain setting, and so on of the reception signal on the reception circuit 63.

The harmonic processing section 142 extracts a harmonic component for each of the channels based on the reception signal of each of the channels.

The signal processing section 143 performs a variety of processes for obtaining a good tomographic image on the reception signal on which the harmonic process has been performed. As the variety of processes, there can be cited a nonlinear compression process such as a logarithmic conversion process for converting the expression format so that the maximum part and the minimum part of the signal strength of the reception signal are easily checked at the same time, a sensitive time control (STC) process for correcting the gain (luminance) in accordance with the propagation time (i.e., the depth) of the reflected wave, and so on. Further, the signal processing section 143 generates a variety of ultrasonic images such as a B-mode image or an M-mode image, and then makes the display section 12 display the ultrasonic images.

Functions and Advantages of First Embodiment

In the present embodiment, the ultrasonic wave transmitting sections 42 and the ultrasonic wave receiving sections 43 are arranged in a line in the X direction. Among these sections, the ultrasonic wave receiving sections 43 are arranged at the intervals L corresponding to the order of the second-order harmonic wave. Further, the ultrasonic wave transmitting sections 42 are configured so that the corresponding number of ultrasonic wave transmitting sections 42 to the order of the high-order harmonic wave, two at a time in the present embodiment, are driven at the same time. Thus, the ultrasonic wave transmitting sections 42 driven at the same time function as a single transmission channel T, and the transmission channels T are arranged at intervals obtained by multiplying the interval L described above by the order of the high-order harmonic wave, namely the intervals 2L.

In such a configuration, since the interval between the transmission channels T is the value obtained by multiplying the interval between the ultrasonic wave receiving sections 43 (i.e., the reception channels R) by the order, the high-order harmonic wave corresponding to the fundamental wave can accurately be detected.

Further, by arranging the ultrasonic wave transmitting sections 42 and the ultrasonic wave receiving sections 43 in a line along the X direction, the ultrasonic device 4 can be miniaturized compared to the configuration in which the transmission line formed of the ultrasonic wave transmitting sections 42 and the reception line formed of the ultrasonic wave receiving sections 43 are arranged in parallel to each other.

Further, in the case in which the ultrasonic device 4 is formed with the same size as in the configuration in which the transmission line and the reception line described above are arranged in parallel to each other in the Y direction (the slicing direction), the dimension in the slicing direction of the transmitting aperture can be enlarged, and the resolution can be improved.

Further, since the ultrasonic wave transmitting sections 42 and the ultrasonic wave receiving sections 43 are arranged in a line along the X direction, the central position P1 of the transmitting aperture and the central position P2 of the receiving aperture can be made closer to each other compared to the configuration in which the transmission line and the reception line described above are arranged in parallel to each other. Therefore, it is possible to suppress the degradation of the resolution due to the central position P1 of the transmitting aperture and the central position P2 of the receiving aperture getting away from each other.

Further, the ultrasonic wave receiving section 43 (the receiving aperture) is disposed at a position overlapping the ultrasonic wave transmitting section 42 (the transmitting aperture) in the projection view along the X direction. In other words, the ultrasonic wave receiving section 43 is disposed so as to be included in the ultrasonic wave transmitting section 42 in the projection view described above. In such a configuration, it is possible to improve the resolution compared to the case in which at least a part of the ultrasonic wave receiving section 43 is disposed at a position not overlapping the ultrasonic wave transmitting section 42 in the projection view described above.

In the present embodiment, the ultrasonic wave transmitting sections 42 and the ultrasonic wave receiving sections 43 are arranged alternately, the ultrasonic wave transmitting sections 42 are arranged at predetermined intervals, and the ultrasonic wave receiving sections 43 are arranged at predetermined intervals.

In such a configuration, the fundamental wave as a composite wave of the ultrasonic waves transmitted from the respective ultrasonic wave transmitting sections 42 can more appropriately be transmitted compared to the case in which the interval between the ultrasonic wave transmitting section 42 varies in the arrangement direction. For example, the fundamental wave having the wave front perpendicular to the propagation direction can more surely be formed.

Further, in the present embodiment, in the Y direction, the dimension of the ultrasonic wave transmitting section 42 is larger than the dimension of the ultrasonic wave receiving section 43. In other words, the size of the ultrasonic wave receiving section 43 is smaller than the size of the ultrasonic wave transmitting section 42.

Here, if the dimension of the ultrasonic wave transmitting section 42 in the slicing direction (the Y direction) is enlarged, the ultrasonic wave can more appropriately be converged. However, in the case of arranging the ultrasonic wave transmitting sections 42 and the ultrasonic wave receiving sections 43 in two lines, if the size of the ultrasonic wave transmitting section 42 is enlarged, the distance in the slicing direction between the central position P1 of the ultrasonic wave transmitting section 42 and the central position P2 of the ultrasonic wave receiving section 43 increases. Therefore, it results that the transmission wave is transmitted with the tilt toward the ultrasonic wave receiving section 43, and there is a possibility that the resolution is degraded.

In contrast, in the present embodiment, since the ultrasonic wave transmitting sections 42 and the ultrasonic wave receiving section 43 are arranged in a line along the X direction, the dimension of the ultrasonic wave transmitting section 42 in the slicing direction can be enlarged without changing the central positions in the slicing direction (the Y direction) of the ultrasonic wave transmitting sections 42 and the ultrasonic wave receiving sections 43. Therefore, the possibility of the degradation of the resolution described above does not exist, and moreover, the resolution can be improved by enlarging the size of the ultrasonic wave transmitting section 42 as described above. Further, by decreasing the size of the ultrasonic wave receiving section 43, the reflected wave from the convergence region of the fundamental wave can more appropriately be received by the ultrasonic wave receiving sections 43, and thus, the resolution can be improved.

In the present embodiment, the central position P1 of the ultrasonic wave transmitting section 42 and the central position P2 of the ultrasonic wave receiving section 43 are located on the same imaginary line O1. Therefore, an amount of the shift between the centers of the transmitting aperture and the receiving aperture can be made smaller, and thus, the resolution can be improved compared to the case of arranging the ultrasonic wave transmitting sections 42 and the ultrasonic wave receiving sections 43 in two lines.

Further, since the positions of the centers of the transmitting aperture and the receiving aperture in the Y direction coincide with each other, the propagation directions of the transmitted wave and the reflected wave can be made roughly parallel to each other, and thus, the resolution can further be improved.

Further, in the ultrasonic device 4 according to the present embodiment, the two ultrasonic wave transmitting sections 42 constituting the single transmission channel T are connected to the same terminal. Thus, by inputting the drive signal to the terminal, it is possible to drive the two ultrasonic wave transmitting sections 42 described above at the same time. Therefore, compared to the case of inputting individual drive signals respectively to the two ultrasonic wave transmitting sections 42 described above to drive the two ultrasonic wave transmitting sections 42 described above at the same time, the process of synchronizing the drive timing of the two ultrasonic wave transmitting sections 42 and so on can be eliminated, and thus simplification of the control process can be achieved.

In the present embodiment, the ultrasonic wave transmitting sections 42 and the ultrasonic wave receiving sections 43 are arranged in a line along the X direction, and are connected to the terminals disposed on both of the +Y side and the −Y side. In such a configuration, the ultrasonic wave transmitting sections 42 and the ultrasonic wave receiving sections 43 can more surely be driven with desired characteristics compared to the configuration in which the ultrasonic wave transmitting sections 42 and the ultrasonic wave receiving sections 43 are connected to terminals disposed only on either of the +Y side and the −Y side. Specifically, although there is a possibility that the voltage drops with the distance from the terminal due to the internal resistance of the ultrasonic wave transmitting section 42, and the piezoelectric element cannot be driven with the desired characteristics, since in the present embodiment, the voltage is applied from the terminals disposed on the both sides in the Y direction, the problem described above can be inhibited from occurring.

It should be noted that in the case in which the ultrasonic wave transmitting sections 42 and the ultrasonic wave receiving sections 43 are disposed side by side in the Y direction, it is difficult to adopt the configuration described above. In contrast, in the present embodiment, since the ultrasonic wave transmitting sections 42 and the ultrasonic wave receiving sections 43 are arranged in a line, it is easy to draw the signal lines from the ultrasonic wave transmitting sections 42 and the ultrasonic wave receiving sections 43 toward both of the +Y side and the −Y side.

Modified Example of First Embodiment

Figure 8:
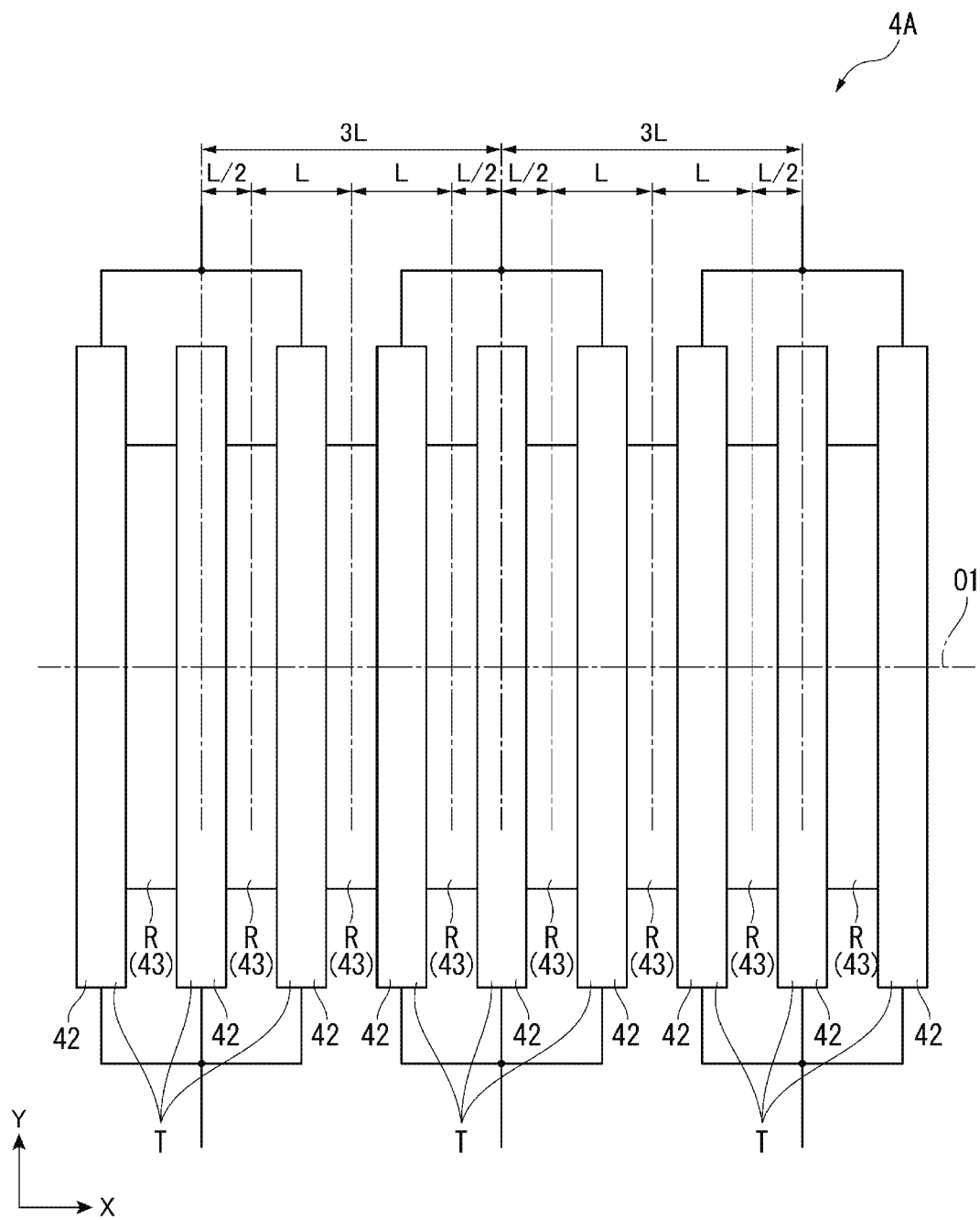
FIG. 8 is a plan view showing a schematic configuration of an ultrasonic device according to a modified example of the first embodiment.

FIG. 8 is a diagram schematically showing an ultrasonic device according to a modified example of the first embodiment.

Although in the first embodiment, there is illustrated the configuration in which the ultrasonic device 4 has the second-order harmonic wave corresponding to the fundamental wave as the reception object, and makes the two ultrasonic wave transmitting sections 42 adjacent in the X direction to each other function as the single transmission channel T, the invention is not limited to this configuration.

In the ultrasonic device 4A shown in FIG. 8, a third-order harmonic wave corresponding to the fundamental wave is used as the reception object, and three ultrasonic wave transmitting sections 42 adjacent in the X direction to each other are made to function as a single transmission channel T. Specifically, the three ultrasonic wave transmitting sections 42 are connected to the common signal terminals SA, SB (see FIG. 4). In the ultrasonic device 4A, the transmission pitch becomes three times as long as the reception pitch, and thus, the third-order harmonic wave with respect to the fundamental wave can be received with high accuracy.

It should be noted that in the present modified example, the reception pitch and the size of the vibrating film of the receiving element 431 are set in accordance with the wavelength of the third-order harmonic wave.

As described above, the third-order harmonic wave or a higher-order harmonic wave can be set as the reception object. It should be noted that in the case of setting the n-th-order harmonic wave as the reception object, the single transmission channel is formed of a set of ultrasonic wave transmitting sections 42 consisting of n ultrasonic wave transmitting sections 42 adjacent to each other. Further, defining the dimension in the X direction of the transmitting aperture and the receiving aperture as d, the scanning angle as θ, the wavelength of the fundamental wave as λ, the relationship expressed by Formula (4) described below exists between the transmission pitch Ln and the dimension d of each of the apertures, and the dimension d described above is set so as to fulfill the grating lobe condition, namely Formula (5) described below.

$$Ln = 2nd \quad (4)$$

$$d < \lambda/2n(1+\sin\theta) \quad (5)$$

Second Embodiment

Then, a second embodiment according to the invention will be described.

In the ultrasonic measurement apparatus according to the first embodiment, in order to set a harmonic wave with a predetermined order as the reception object, and to make a plurality of ultrasonic wave transmitting sections function as a single transmission channel, the plurality of ultrasonic wave transmitting sections is connected to the common terminals.

In contrast, in the second embodiment, the ultrasonic measurement apparatus is different from the first embodiment in the point that a plurality of harmonic waves with respective orders is set as the reception object, and there is adopted a configuration in which the transmission pitch can be changed in accordance with the order of the harmonic wave as the reception object.

It should be noted that in the present embodiment, although there is described an example of setting the second-order harmonic wave and the third-order harmonic wave as the reception object, the fourth-order harmonic wave or a higher-order harmonic wave can also be set as the reception object, or three or more types of harmonic waves with respective orders can be set as the reception object.

Further, in the following explanation, the constituents substantially the same as those of the first embodiment are denoted by the same reference symbols, and the explanation thereof will be omitted or simplified.

Figure 9:
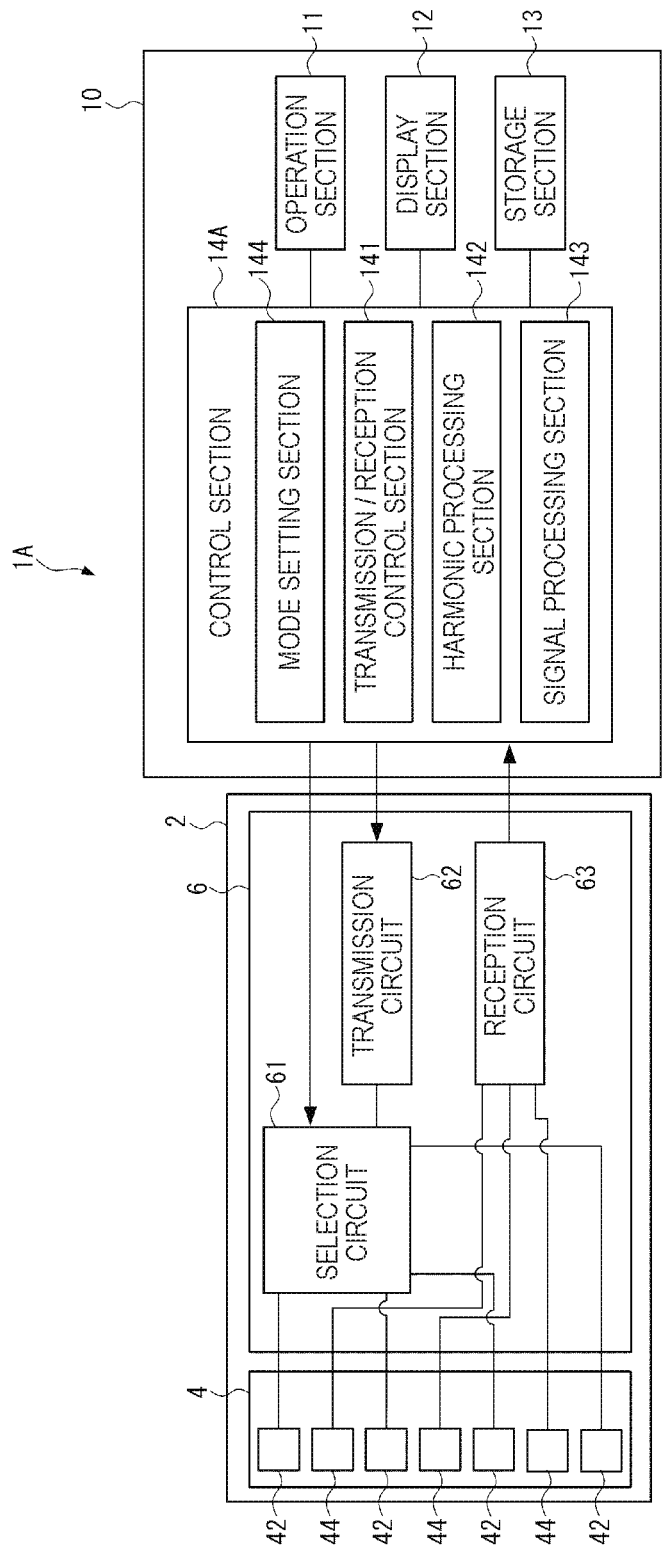
FIG. 9 is a block diagram showing a schematic configuration of an ultrasonic measurement apparatus according to a second embodiment of the invention.

FIG. 9 is a block diagram showing a schematic configuration of an ultrasonic measurement apparatus 1A according to the second embodiment. Further, FIG. 10 is a diagram schematically showing a general configuration of an ultrasonic device 4B equipped with the ultrasonic wave transmitting sections 42 and ultrasonic wave receiving sections 44.

In the ultrasonic device 4B, the ultrasonic wave transmitting sections 42 are configured so as to be connected to the respective signal terminals SA, SB (see FIG. 4) different from each other to thereby be able to individually be driven.

Figure 10:
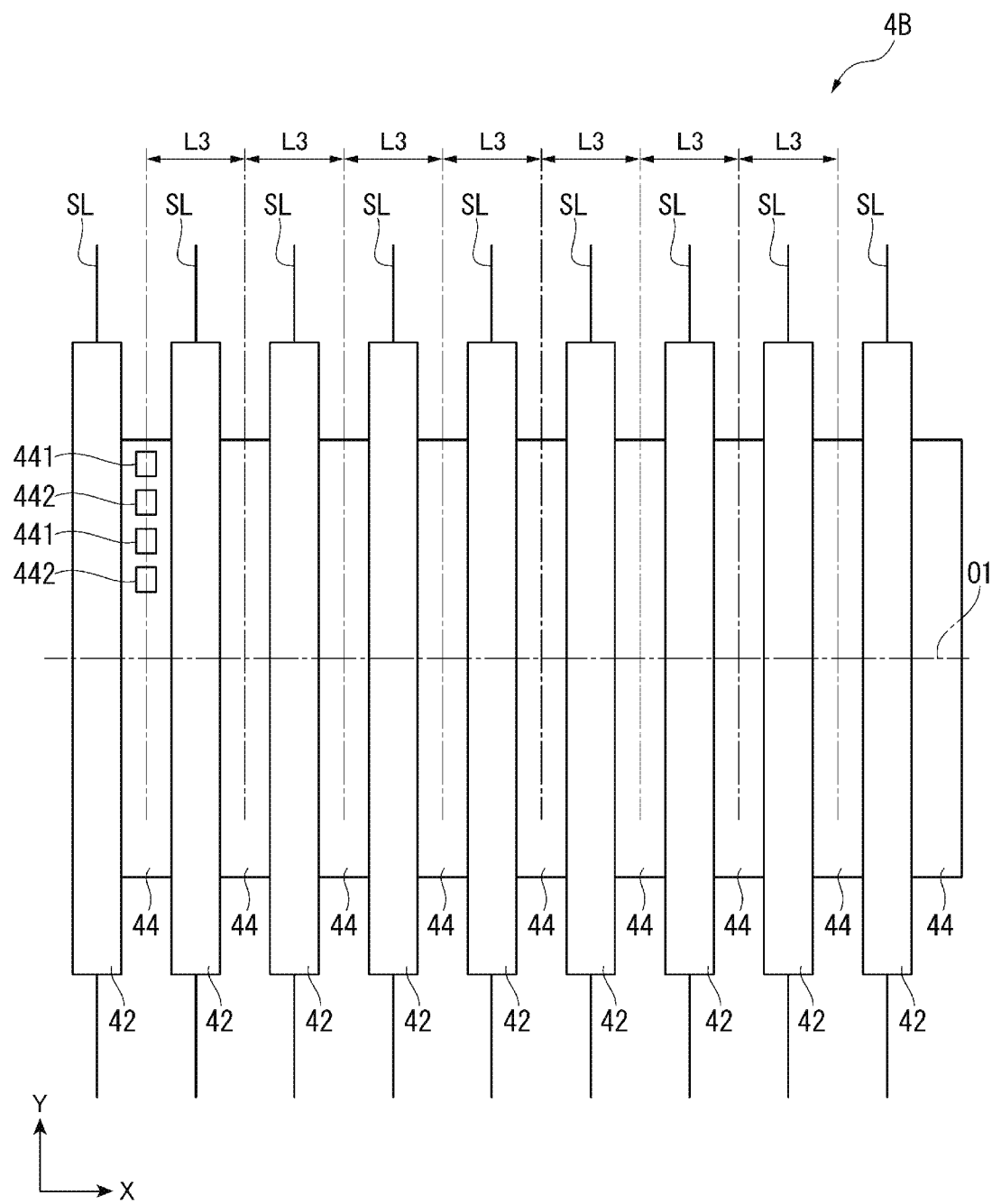
FIG. 10 is a plan view showing a schematic configuration of an ultrasonic device according to the second embodiment.

The ultrasonic wave receiving sections 44 takes the second-order harmonic wave and the third-order harmonic wave as the plurality of high-order harmonic waves to be the reception object, and each have a plurality of receiving elements 441, 442 as shown in FIG. 10, and the first receiving elements 441 and the second receiving elements 442 are alternately arranged in the Y direction.

The first receiving elements 441 have the sensitivity corresponding to the desired measurement accuracy with respect to the second-order harmonic wave. Specifically, in the first receiving element 441, the size and the film thickness of the vibrating film, the characteristics of the piezoelectric element, and so on are set so that the ultrasonic wave in the frequency band of the second-order harmonic wave can be detected with the desired sensitivity.

The second receiving elements 442 have the sensitivity corresponding to the desired measurement accuracy with respect to the third-order harmonic wave. Specifically, the second receiving elements 442 are configured so as to be able to detect the ultrasonic wave in the frequency band of the third-order harmonic wave with the desired sensitivity. It should be noted that the first receiving elements 441 and the second receiving elements 442 are connected to the respective terminals different from each other. Thus, it is possible to individually detect the detection signal from the first receiving elements 441 and the detection signal from the second receiving elements 442.

It should be noted that the ultrasonic wave receiving sections 44 can also be configured including the receiving elements capable of receiving both of the second-order harmonic wave and the third-order harmonic wave. In this case, the size of the vibrating film and the film thickness, the characteristics of the piezoelectric elements, and so on in the receiving elements are set so that the frequency band, which can be received by the receiving elements, includes the frequency band of the second-order harmonic wave and the frequency band of the third-order harmonic wave.

The reception pitch is set in accordance with the highest-order harmonic wave of the high-order harmonic waves to be the reception object. In the present embodiment, the reception pitch L3 corresponding to the third-order harmonic wave is set. Thus, the harmonic waves with lower orders than the highest order can also be received.

As shown in FIG. 9, the selection circuit 61 selects the ultrasonic wave transmitting sections 42 to be connected to the transmission circuit 62 based on the control by the control device 10. It should be noted that in the present embodiment, by selecting a plurality of ultrasonic wave transmitting sections 42 and then outputting the same drive signal to the ultrasonic wave transmitting sections 42 thus selected, the ultrasonic wave transmitting sections 42 thus selected are made to function as a single transmission channel T.

In the present embodiment, the control section 14A functions as the transmission/reception control section 141, the harmonic processing section 142, the signal processing section 143, and a mode setting section 144.

The transmission/reception control section 141 selects the ultrasonic wave transmitting section 42 to be the input object of the drive signal from the transmission circuit. In the present embodiment, the selection control section selects the ultrasonic wave transmitting sections 42 to be driven at the same time out of the ultrasonic wave transmitting sections 42 in each of the case of receiving the second-order harmonic wave (a second-order reception mode) and the case of receiving the third-order harmonic wave (a third-order reception mode).

The mode setting section 144 sets the transmission/reception mode of the ultrasonic wave to either of the second-order reception mode and the third-order reception mode described above. The mode setting section 144 sets the transmission/reception mode designated by, for example, a selection operation of the mode by the user with the operation section 11.

The transmission/reception control section 141 performs the control of making the selection circuit 61 select the ultrasonic wave transmitting sections 42 to be the driving object in accordance with the transmission/reception mode set by the mode setting section 144.

Here, the ultrasonic wave transmitting sections 42 are numbered in an ascending order from the −X side toward the +X side to be denoted by first transmitting section 42 through N-th transmitting section 42.

In the case in which the transmission/reception mode is set to the second-order reception mode, the (2j−1)-th transmitting section 42 and the 2j-th transmitting section 42 are driven at the same time to thereby function as j-th transmission channel Tj (note that $1 \leq j \leq jmax$, $2jmax=N$, and j and jmax are integers). In this case, the transmission pitch becomes twice as long as the reception pitch, and thus, the second-order harmonic wave can accurately be obtained.

Further, in the case in which the transmission/reception mode is set to the third-order reception mode, the (3k−2)-th transmitting section 42, the (3k−1)-th transmitting section 42, and the 3k-th transmitting section 42 are driven at the same time to thereby function as k-th transmission channel Tk (note that $1 \leq k \leq kmax$, $3kmax=N$, and k and kmax are integers). In this case, the transmission pitch becomes three times as long as the reception pitch, and thus, the third-order harmonic wave can accurately be obtained.

Ultrasonic Measurement Process

Figure 11:
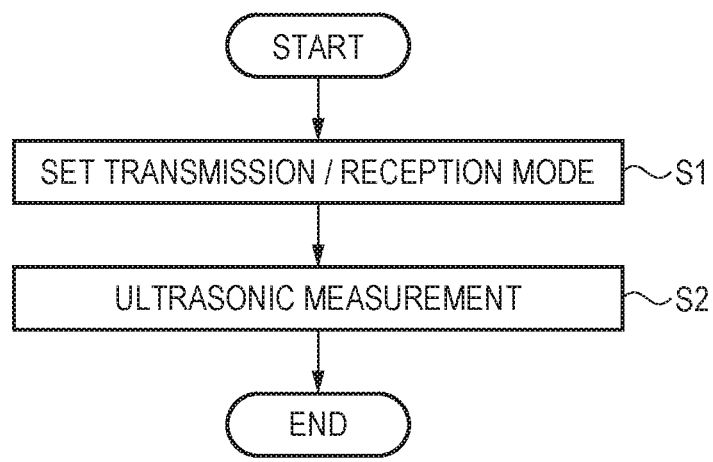
FIG. 11 is a flowchart showing an ultrasonic measurement process according to the second embodiment.

FIG. 11 is a flowchart showing an example of the ultrasonic measurement process.

As shown in FIG. 11, the mode setting section 144 firstly sets (step S1) the transmission/reception mode based on the operation instruction by the user.

Further, the transmission/reception control section 141 drives the ultrasonic probe 2 based on the transmission/reception mode thus set to thereby make the ultrasonic measurement apparatus 1A perform the ultrasonic measurement (step S2).

For example, in the case in which the transmission/reception mode is set to the second-order reception mode, the transmission/reception control section 141 controls the selection circuit 61 to drive the two ultrasonic wave transmitting sections 42 adjacent to each other as a single transmission channel T. In the case of changing the scanning direction due to a sector scan or the like, the (2k−1)-th transmitting section 42 and the 2k-th transmitting section 42 constituting each of the transmission channels T are driven at the same time, and further, the ultrasonic wave is transmitted while sequentially delaying the transmission channels started from the first transmission channel T1. Thus, it is possible to drive the ultrasonic device 4B so that the transmission pitch becomes twice as long as the reception pitch.

It should be noted that in the case in which a start instruction of the ultrasonic measurement has been received without providing the instruction related to the setting of the transmission/reception mode, the control section 14 makes the ultrasonic measurement be performed using the transmission/reception mode currently set without performing the setting of the transmission/reception mode.

Further, in the case in which the control section receives the setting instruction of the transmission/reception mode during the ultrasonic measurement, the control section 14 terminates the ultrasonic measurement process, then sets the transmission/reception mode, and then performs the ultrasonic measurement based on the transmission/reception mode thus set.

Functions and Advantages of Second Embodiment

In the present embodiment, the selection circuit 61 selects the ultrasonic wave transmitting sections 42 to be driven at the same time based on the control by the control section 14A so that the interval between the transmission channels T becomes the interval obtained by multiplying the interval L between the reception channels R by the order of the high-order harmonic wave to be the reception object.

In such a configuration, the same advantages as in the first embodiment can be obtained, and further, it is possible to set a plurality of high-order harmonic waves of the respective orders to the reception object, and to receive the respective high-order harmonic waves with high accuracy. Specifically, by appropriately selecting the ultrasonic wave transmitting sections 42 to be driven at the same time so that the intervals of the transmission channels T become 2L in the case of setting the second-order harmonic wave as the reception object as described above, or the intervals of the transmission channels T become 3L in the case of setting the third-order harmonic wave as the reception object, it is possible to set the transmission pitch corresponding to the order of the high-order harmonic wave. Therefore, it is possible to accurately receive the plurality of high-order harmonic waves with the respective orders with the single ultrasonic device 4A.

Further, in the present embodiment, the ultrasonic wave receiving sections 44 are each provided with the receiving elements corresponding respectively to the plurality of orders. Thus, even in the case of setting the plurality of high-order harmonic waves with the respective orders as the reception object, the detection accuracy of the harmonic waves with the respective orders can be improved.

It should be noted that in the case in which the receiving elements 431 are configured so as to be able to receive the fundamental wave, by individually driving the ultrasonic wave transmitting sections 42, the fundamental wave can also be set as the reception object, and thus, the convenience of the ultrasonic measurement apparatus can be enhanced.

Other Modified Examples

It should be noted that the invention is not limited to each of the embodiments described above, but includes modifications and improvements within a range where the advantages of the invention can be achieved, and configurations, which can be obtained by, for example, arbitrarily combining the embodiments.

Figure 12:
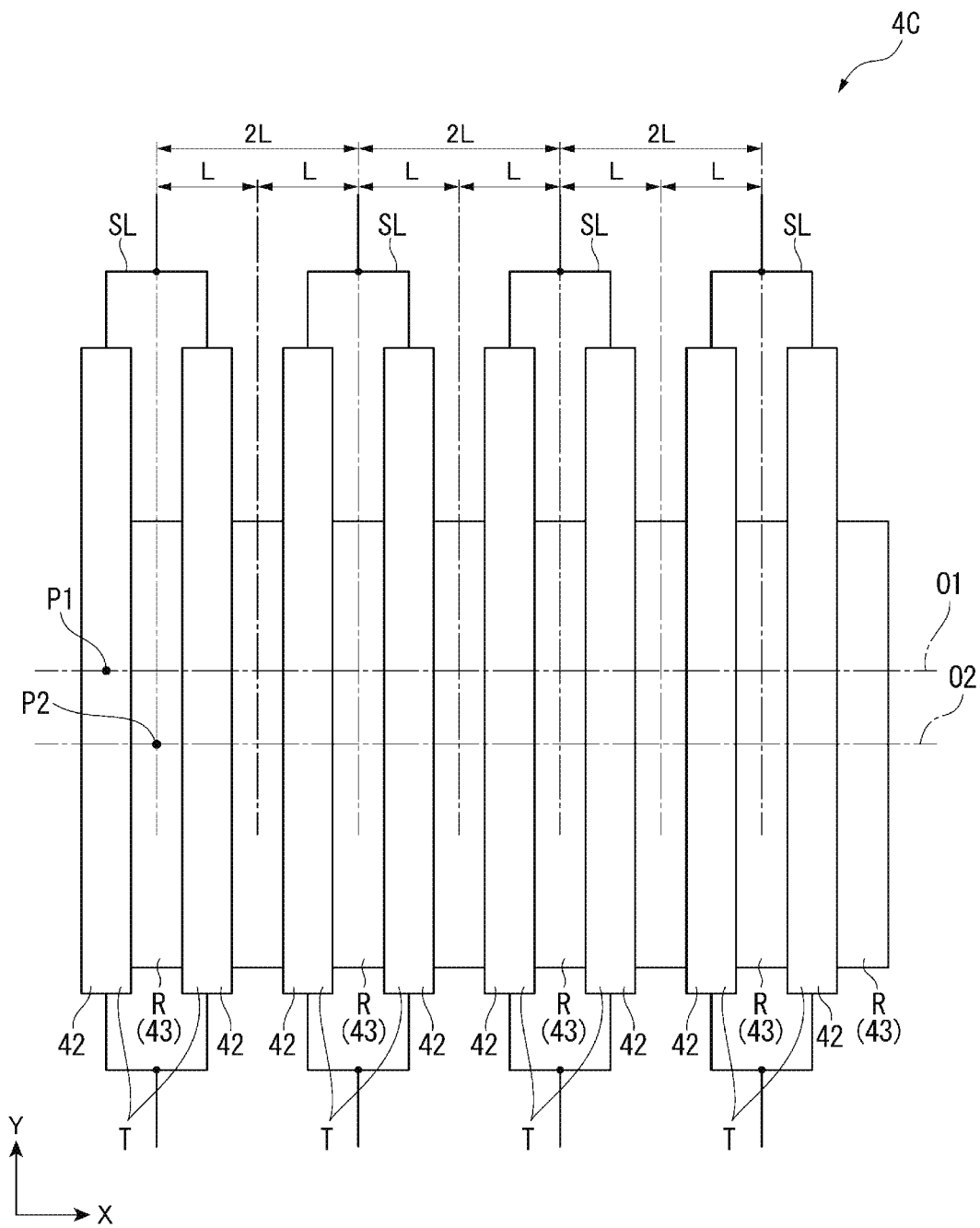
FIG. 12 is a plan view showing a schematic configuration of an ultrasonic device according to a modified example of the invention.

FIG. 12 is a diagram showing a schematic configuration of an ultrasonic device 4C according to a modified example of the invention.

Although in each of the embodiments described above, the central position P1 of the transmitting aperture and the central position P2 of the receiving aperture are located on the same imaginary line O1 parallel to the Y axis, the invention is not limited to this configuration. Specifically, it is possible to adopt a configuration in which the central position P2 of the receiving aperture is located on an imaginary line O2 different from the imaginary line O1 on which the central position P1 of the transmitting aperture is located. In this case, it is sufficient for the imaginary line O2 to overlap at least the transmitting aperture, and thus, it is possible to suppress the degradation of the resolution compared to a configuration in which the transmitting aperture and the receiving aperture are arranged side by side in the Y direction. Further, it is possible to suppress the degradation of the resolution while achieving miniaturization of the ultrasonic device.

Although in each of the embodiments, the ultrasonic wave transmitting section 42 and the ultrasonic wave receiving section 43 are the same in dimension in the X direction, the invention is not limited to this configuration, but the dimensions can be different from each other. Even in this case, since the ultrasonic wave transmitting sections 42 and the ultrasonic wave receiving sections 43 each having the predetermined size are alternately arranged in the X direction as in each of the embodiments described above, the ultrasonic wave transmitting sections 42 and the ultrasonic wave receiving sections 43 can each be arranged at predetermined intervals.

Figure 13:
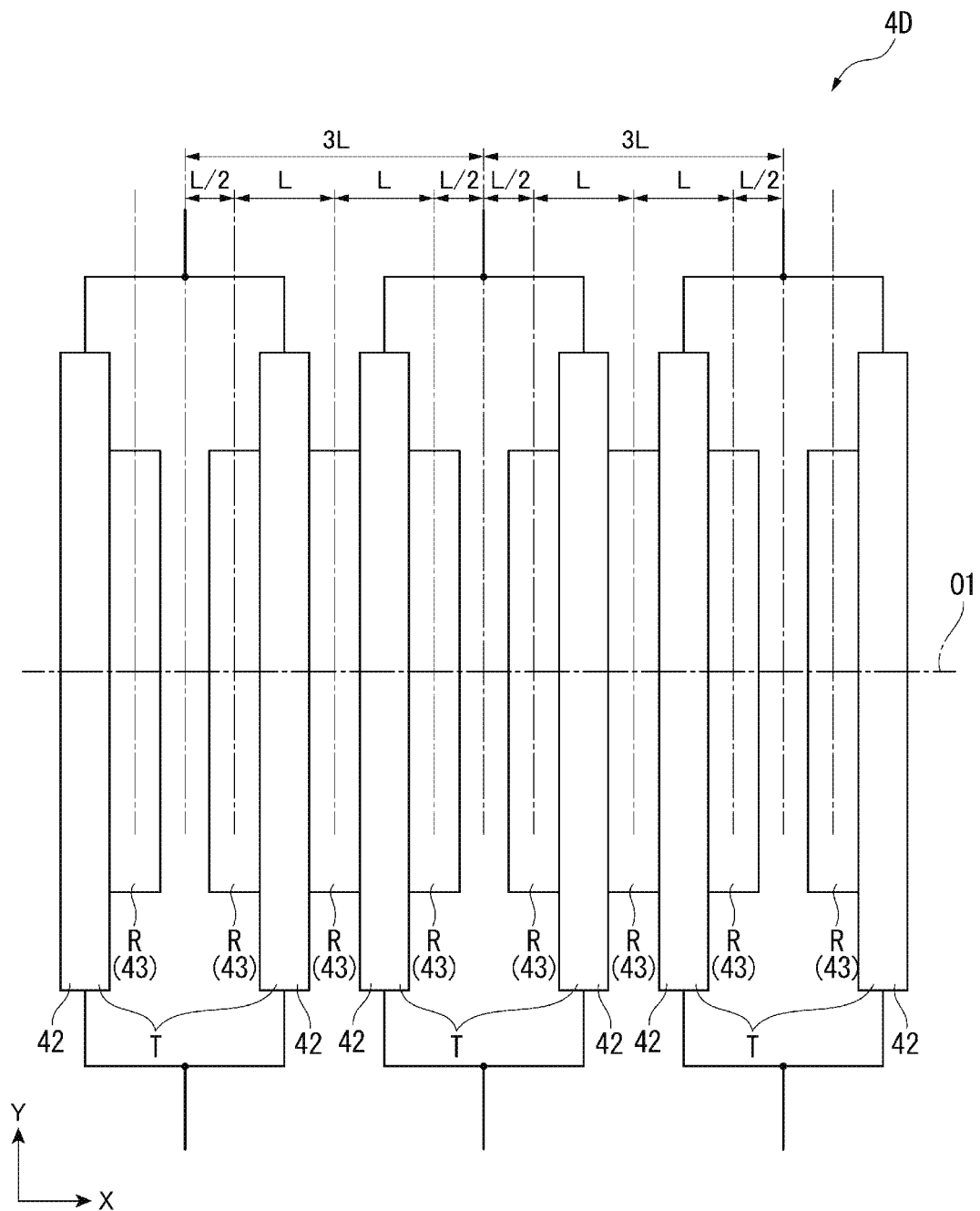
FIG. 13 is a plan view showing a schematic configuration of an ultrasonic device according to a modified example of the invention.

FIG. 13 is a diagram showing a schematic configuration of an ultrasonic device 4D according to a modified example of the invention.

Although in each of the embodiments described above, there is illustrated the configuration in which the ultrasonic wave transmitting sections 42 and the ultrasonic wave receiving sections 43 are arranged alternately in the X direction, the invention is not limited to this configuration. Specifically, it is also possible for the ultrasonic wave receiving sections 43 to be arranged adjacent to each other in at least a part of the area.

FIG. 13 shows, as an example, the ultrasonic device 4D configured so as to be able to receive the third-order harmonic wave. In the ultrasonic device 4D, the reception channels R are arranged at predetermined intervals corresponding to the frequency (the wavelength) of the third-order harmonic wave. In contrast, the transmission channels T is formed of the two ultrasonic wave transmitting sections 42 disposed on both sides in the Y direction of the two reception channels R arranged at a predetermined interval. In such a configuration, the ultrasonic wave receiving sections 43 are consecutively disposed between the two ultrasonic wave transmitting sections 42 in the transmission channel T. In such a configuration, the number of ultrasonic wave transmitting sections 42 can be decreased to thereby simplify the configuration compared to the case in which the transmission channel T is formed of the three ultrasonic wave transmitting sections 42.

It should be noted that although in the ultrasonic device 4D shown in FIG. 13, there is illustrated the configuration in which the two ultrasonic wave receiving sections 43 are disposed between the two ultrasonic wave transmitting sections 42 constituting the transmission channel T, and no ultrasonic wave transmitting section 42 is disposed between the two ultrasonic wave receiving sections 43, the invention is not limited to this configuration. For example, it is also possible that the ultrasonic wave transmitting sections 42 and the ultrasonic wave receiving sections 43 are arranged alternately, and the drive control of the ultrasonic device is performed so that the two ultrasonic wave transmitting sections 42 disposed on the both sides of the two ultrasonic wave receiving sections 43 are selectively driven, and the ultrasonic wave transmitting section 42 disposed between the two ultrasonic wave receiving sections 43 is not driven. The transmission channel T can be configured by configuring the ultrasonic wave transmitting sections 42 so as to be driven individually, and driving a part of the corresponding number of ultrasonic wave transmitting sections 42 to the order of the high-order harmonic wave.

Although in the second embodiment, the two types of first receiving elements 441, 442 are provided, and are configured so as to be able to receive the two high-order harmonic waves different in frequency, the invention is not limited to this configuration, but can adopt a configuration of simultaneously including three or more types of receiving elements for receiving the high-order harmonic waves different in order from each other in a good condition.

Although in each of the embodiments described above, as the ultrasonic device, there is illustrated the configuration of including the one-dimensional array structure in which the transmitting elements 421 constituting the ultrasonic wave transmitting section 42 are driven at the same time, the invention is not limited to this configuration. Specifically, it is also possible for the ultrasonic device to have a two-dimensional array structure in which the transmitting elements 421 are configured so as to be able to be driven individually in one ultrasonic wave transmitting section 42.

Although in each of the embodiments described above, there is illustrated the ultrasonic measurement apparatus taking a part of a living body as the measurement object, the invention is not limited to this example. For example, the invention can be applied to an ultrasonic measurement apparatus taking a variety of types of structures as the measurement object, and for performing the detection of the defects and inspection of aging of the structure. Further, the invention can also be applied to an ultrasonic measurement apparatus taking, for example, a semiconductor package or a wafer as the measurement object, and for detecting the defects of the measurement object.

Besides the above, specific structures to be adopted when implementing the invention can be configured by arbitrarily combining the embodiments and the modified examples described above with each other, or can arbitrarily be replaced with other structures and so on within the range in which the advantages of the invention can be achieved.

The entire disclosure of Japanese Patent Application No. 2015-170531 filed on Aug. 31, 2015 is expressly incorporated by reference herein.

What is claimed is:

1. An ultrasonic device comprising:
   a substrate;
   a plurality of ultrasonic wave transmitting groups disposed on the substrate, each group of the plurality of ultrasonic wave transmitting groups being configured with a plurality of ultrasonic wave transmitting elements, each group of the plurality of ultrasonic wave transmitting groups extending along a first direction so that the plurality of ultrasonic wave transmitting elements in each group of the plurality of ultrasonic wave transmitting groups are serially connected along the first direction, each element of the plurality of ultrasonic wave transmitting elements transmitting a fundamental wave; and
   a plurality of ultrasonic wave receiving groups disposed on the substrate, each group of the plurality of ultrasonic wave receiving groups being configured with a plurality of ultrasonic wave receiving elements, each group of the plurality of ultrasonic wave receiving groups extending along the first direction so that the plurality of ultrasonic wave receiving elements in each group of the plurality of ultrasonic wave receiving groups are serially connected along the first direction, each element of the plurality of ultrasonic wave receiving elements receiving an N-th-order harmonic wave with respect to the fundamental wave,
   wherein the plurality of ultrasonic wave transmitting groups and the plurality of ultrasonic wave receiving groups are alternately arranged along a second direction perpendicular to the first direction so that each group of the plurality of ultrasonic wave transmitting groups and each group of the plurality of ultrasonic wave receiving groups are directly adjacent and parallel to each other,
   a distance in the second direction between adjacent two groups of the plurality of ultrasonic wave receiving groups is a first distance corresponding to an N-th-order of the N-th-order harmonic wave,
   an N group of the plurality of ultrasonic wave transmitting groups is a single unit of a transmission channel, and the plurality of ultrasonic wave transmitting elements of the N group of the plurality of ultrasonic wave transmitting groups are wired with each other, and
   a distance in the second direction between adjacent two channels of the transmission channels is a second distance, and the second distance is N times as long as the first distance.

2. The ultrasonic device according to claim 1, wherein an extending length of each group of the plurality of ultrasonic wave transmitting groups along the first direction is larger than an extending length of each group of the plurality of ultrasonic wave receiving groups along the first direction.

3. The ultrasonic device according to claim 1, wherein the plurality of ultrasonic wave transmitting groups overlaps an imaginary line which passes through a central position in the first direction of each group of the plurality of ultrasonic wave receiving groups, and the imaginary line extends along the second direction.

4. The ultrasonic device according to claim 3, wherein the plurality of ultrasonic wave receiving groups is disposed at a position overlapping the plurality of ultrasonic wave transmitting groups in a projection view along the second direction.

5. An ultrasonic module comprising:
   an ultrasonic device, the ultrasonic device being configured with:
      a substrate;
      a plurality of ultrasonic wave transmitting groups disposed on the substrate, each group of the plurality of ultrasonic wave transmitting groups being configured with a plurality of ultrasonic wave transmitting elements, each group of the plurality of ultrasonic wave transmitting groups extending along a first direction so that the plurality of ultrasonic wave transmitting elements in each group of the plurality of ultrasonic wave transmitting groups are serially connected along the first direction, each element of the plurality of ultrasonic wave transmitting elements transmitting a fundamental wave; and
      a plurality of ultrasonic wave receiving groups disposed on the substrate, each group of the plurality of ultrasonic wave receiving groups being configured with a plurality of ultrasonic wave receiving elements, each group of the plurality of ultrasonic wave receiving groups extending along the first direction so that the plurality of ultrasonic wave receiving elements in each group of the plurality of ultrasonic wave receiving groups are serially connected along the first direction, each element of the plurality of ultrasonic wave receiving elements receiving an N-th-order harmonic wave with respect to the fundamental wave; and
   a circuit board on which the ultrasonic device is disposed,
   wherein the plurality of ultrasonic wave transmitting groups and the plurality of ultrasonic wave receiving groups are alternately arranged along a second direction perpendicular to the first direction so that each group of the plurality of ultrasonic wave transmitting groups and each group of the plurality of ultrasonic wave receiving groups are directly adjacent and parallel to each other,
   a distance in the second direction between adjacent two groups of the plurality of ultrasonic wave receiving groups is a first distance corresponding to an N-th-order of the N-th-order harmonic wave, an N group of the plurality of ultrasonic wave transmitting groups is a single unit of a transmission channel, and the plurality of ultrasonic wave transmitting elements of the N group of the plurality of ultrasonic wave transmitting groups are wired with each other, and a distance in the second direction between adjacent two channels of the transmission channels is a second distance, and the second distance is N times as long as the first distance.

6. The ultrasonic module according to claim 5, wherein an extending length of each group of the plurality of ultrasonic wave transmitting groups along the first direction is larger than an extending length of each group of the plurality of ultrasonic wave receiving groups along the first direction.

7. The ultrasonic module according to claim 5, wherein the plurality of ultrasonic wave transmitting groups overlaps an imaginary line which passes through a central position in the first direction of each group of the plurality of ultrasonic wave receiving groups, and the imaginary line extends along the second direction.

8. The ultrasonic module according to claim 7, wherein the plurality of ultrasonic wave receiving groups is disposed at a position overlapping the plurality of ultrasonic wave transmitting groups in a projection view along the second direction.

9. An ultrasonic measurement apparatus comprising:

an ultrasonic device, the ultrasonic device being configured with:

a substrate;

a plurality of ultrasonic wave transmitting groups disposed on the substrate, each group of the plurality of ultrasonic wave transmitting groups being configured with a plurality of ultrasonic wave transmitting elements, each group of the plurality of ultrasonic wave transmitting groups extending along a first direction so that the plurality of ultrasonic wave transmitting elements in each group of the plurality of ultrasonic wave transmitting groups are serially connected along the first direction, each element of the plurality of ultrasonic wave transmitting elements transmitting a fundamental wave; and a plurality of ultrasonic wave receiving groups disposed on the substrate, each group of the plurality of ultrasonic wave receiving groups being configured with a plurality of ultrasonic wave receiving elements, each group of the plurality of ultrasonic wave receiving groups extending in the first direction, each element of the plurality of ultrasonic wave receiving elements receiving an N-th-order harmonic wave with respect to the fundamental wave; and a controller configured to execute a program so as to control the ultrasonic device, wherein the plurality of ultrasonic wave transmitting groups and the plurality of ultrasonic wave receiving groups are alternately arranged along a second direction perpendicular to the first direction so that each group of the plurality of ultrasonic wave transmitting groups and each group of the plurality of ultrasonic wave receiving groups are directly adjacent and parallel to each other, a distance in the second direction between adjacent two groups of the plurality of ultrasonic wave receiving groups is a first distance corresponding to an N-th-order of the N-th-order harmonic wave, an N group of the plurality of ultrasonic wave transmitting groups is a single unit of a transmission channel, and the plurality of ultrasonic wave transmitting elements of the N group of the plurality of ultrasonic wave transmitting groups are wired with each other, and a distance in the second direction between adjacent two channels of the transmission channels is a second distance, and the second distance is N times as long as the first distance.

10. The ultrasonic measurement apparatus according to claim 9, wherein an extending length of each group of the plurality of ultrasonic wave transmitting groups along the first direction is larger than an extending length of each group of the plurality of ultrasonic wave receiving groups along the first direction.

11. The ultrasonic measurement apparatus according to claim 9, wherein the plurality of ultrasonic wave transmitting groups overlaps an imaginary line which passes through a central position in the first direction of each group of the plurality of ultrasonic wave receiving groups, and the imaginary line extends along the second direction.

12. The ultrasonic measurement apparatus according to claim 11, wherein the plurality of ultrasonic wave receiving groups is disposed at a position overlapping the plurality of ultrasonic wave transmitting groups in a projection view along the second direction.

* * * * *